United States Patent
Yoshinaga et al.

(10) Patent No.: US 7,935,526 B2
(45) Date of Patent: May 3, 2011

(54) HERG CHANNEL-EXPRESSING CELL

(75) Inventors: Takashi Yoshinaga, Tsukuba (JP); Toru Arai, Tsukuba (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 1193 days.

(21) Appl. No.: 10/595,858

(22) PCT Filed: Nov. 17, 2004

(86) PCT No.: PCT/JP2004/017441
§ 371 (c)(1),
(2), (4) Date: Jul. 11, 2006

(87) PCT Pub. No.: WO2005/047500
PCT Pub. Date: May 26, 2005

(65) Prior Publication Data
US 2006/0292546 A1 Dec. 28, 2006

(30) Foreign Application Priority Data
Nov. 17, 2003 (JP) .................................. 2003-387255

(51) Int. Cl.
*C12N 5/10* (2006.01)
(52) U.S. Cl. ........................................................ 435/325
(58) Field of Classification Search .................... None
See application file for complete search history.

(56) References Cited

U.S. PATENT DOCUMENTS
5,512,421 A  4/1996 Burns et al.

FOREIGN PATENT DOCUMENTS
WO  WO-02/19966 A2  3/2002
WO  WO-03/027634 A2  4/2003

OTHER PUBLICATIONS

"High Throughput Ion-Channel Pharmacology: Planar-Array-Based Voltage Clamp" by Kiss et al., Assay and Drug Development Technologies, vol. 1, No. 1-2, 2003, pp. 127-135.
Nuss, H. B., et al, Overexpression of a human potassium channel suppresses cardiac hyperexcitability in rabbit ventricular myocytes, The Journal of Clinical Investigation, Mar. 1999, vol. 103, No. 6, p. 889-896.
Hoppe, U. C., et al., Distinct gene-specific mechanism of arrhythmia revealed by cardiac gene transfer of two long QT disease genes, HERG and KCNE1, PNAS, Apr. 24, 2001, vol. 98, No. 9, p. 5335-5340.
Pfohl, J. L., et al., Society for Neuroscience Abstracts, 2001, vol. 27, No. 2, p. 2149.
Morgenstern, J. P. et al. "Advanced mammalian gene transfer: high titre retrovirla vectors with multiple drug selection markers and a complementary helper-free packaging cell line." Nucleic Acids Research, Oxford University Press, Surrey GB, vol. 19, No. 12, 1990, p. 3587-3596.
"ViraPowerTM Lentiviral Expression System." 2002, Invitrogen Corporation. (http://www.invitrogen.com/content/sfs/brochures/710_021387_viralPowerAnnounc.pdf).
Schroeder, Kirk S. "An interview with Kirk S. Schroeder, President, Essen Instruments." Assay and Drug Development Technologies. Nov. 2002, vol. 1, No. 1, pt 1. Nov. 2002 pp. 3-8.
Bennett, P. B. et al. "Trends in Ion-Channel Drug Discovery: Advances in Screening Technologies." Trends in Biotechnology, Elsevier Publications, Cambridge, GB, vol. 21, No. 12. Oct. 28, 2003 (pp. 563-569).
Dull et al., "A Third-Generation Lentivirus Vector with a Conditional Packaging System", J. of Virology, 72(11):8463-8471(1998).
Pearlstein et al., "Characterization of HERG Potassium Channel Inhibition Using CoMSiA 3D QSAR and Homology Modeling Approaches", Bioorganic & Medicinal Chemistry Letters 13:1829-1835 (2003).
Schroeder et al., "IonWorks™ HT: A New High-Throughput Electrophysiology Measurement Platform", Journal of Biomolecular Screening 8(1):50-64 (2003).
Japanese Office Action for Application No. 2005-515507, dated Mar. 2, 2010 (with English translation) 9 pages.
Japanese Office Action for Application No. 2005-515507, dated Jun. 8, 2010 (with English translation) 9 pages.

*Primary Examiner* — Michael Pak
(74) *Attorney, Agent, or Firm* — Fish & Richardson P.C.

(57) ABSTRACT

It is an object of the present invention to establish a method of establishing a cell with a remarkably high hERG channel expression level for use in predicting adverse effects based on hERG channel inhibition in research and development of drugs, and to thereby establish a highly sensitive and high throughput evaluation method.

By inserting a hERG gene into a retrovirus vector plasmid or lentivirus vector plasmid to thereby prepare a virus vector, concentrating the vector by ultracentrifugation if necessary, transferring the hERG gene into cells and expressing hERG channels therein, it has become possible to secure an expression level effective in measurements using a fully automated high throughput patch clamp system or dyes.

15 Claims, 20 Drawing Sheets

A

B

C

D

E

SEQUENCE LISTING

```
<160> NUMBER OF SEQ ID NOS: 13

<210> SEQ ID NO 1
<211> LENGTH: 4070
<212> TYPE: DNA
<213> ORGANISM: Homo Sapiens
<220> FEATURE:
<221> NAME/KEY: CDS
<222> LOCATION: (184)..(3660)

<400> SEQUENCE: 1
acgcggcctg ctcaggcctc cagcggccgg tcggagggga ggcgggaggc gagcgaggac      60
ccgcgcccgc agtccagtct gtgcgcgccc gtgctcgctt ggcgcggtgc gggaccagcg     120
ccggccaccc gaagcctagt gcgtcgccgg gtgggtgggc ccgcccggcg ccatgggctc     180 agg atg ccg gtg cgg agg ggc cac gtc gcg ccg cag aac acc ttc ctg      228
    Met Pro Val Arg Arg Gly His Val Ala Pro Gln Asn Thr Phe Leu
    1               5                   10                  15 gac acc atc atc cgc aag ttt gag ggc cag agc cgt aag ttc atc atc      276
Asp Thr Ile Ile Arg Lys Phe Glu Gly Gln Ser Arg Lys Phe Ile Ile
                20                  25                  30 gcc aac gct cgg gtg gag aac tgc gcc gtc atc tac tgc aac gac ggc      324
Ala Asn Ala Arg Val Glu Asn Cys Ala Val Ile Tyr Cys Asn Asp Gly
            35                  40                  45 ttc tgc gag ctg tgc ggc tac tcg cgg gcc gag gtg atg cag cga ccc      372
Phe Cys Glu Leu Cys Gly Tyr Ser Arg Ala Glu Val Met Gln Arg Pro
        50                  55                  60 tgc acc tgc gac ttc ctg cac ggg ccg cgc acg cag cgc cgc gct gcc      420
Cys Thr Cys Asp Phe Leu His Gly Pro Arg Thr Gln Arg Arg Ala Ala
    65                  70                  75 gcg cag atc gcg cag gca ctg ctg ggc gcc gag gag cgc aaa gtg gaa      468
Ala Gln Ile Ala Gln Ala Leu Leu Gly Ala Glu Glu Arg Lys Val Glu
80                  85                  90                  95
```

-continued

| | |
|---|---|
| atc gcc ttc tac cgg aaa gat ggg agc tgc ttc cta tgt ctg gtg gat<br>Ile Ala Phe Tyr Arg Lys Asp Gly Ser Cys Phe Leu Cys Leu Val Asp<br>100                                105                       110 | 516 |
| gtg gtg ccc gtg aag aac gag gat ggg gct gtc atc atg ttc atc ctc<br>Val Val Pro Val Lys Asn Glu Asp Gly Ala Val Ile Met Phe Ile Leu<br>           115                         120                       125 | 564 |
| aat ttc gag gtg gtg atg gag aag gac atg gtg ggg tcc ccg gct cat<br>Asn Phe Glu Val Val Met Glu Lys Asp Met Val Gly Ser Pro Ala His<br>130                                135                       140 | 612 |
| gac acc aac cac cgg ggc ccc ccc acc agc tgg ctg gcc cca ggc cgc<br>Asp Thr Asn His Arg Gly Pro Pro Thr Ser Trp Leu Ala Pro Gly Arg<br>     145                       150                       155 | 660 |
| gcc aag acc ttc cgc ctg aag ctg ccc gcg ctg ctg gcg ctg acg gcc<br>Ala Lys Thr Phe Arg Leu Lys Leu Pro Ala Leu Leu Ala Leu Thr Ala<br>160                       165                   170                   175 | 708 |
| cgg gag tcg tcg gtg cgg tcg ggc ggc gcg ggc ggc gcg ggc gcc ccg<br>Arg Glu Ser Ser Val Arg Ser Gly Gly Ala Gly Gly Ala Gly Ala Pro<br>                     180                       185                   190 | 756 |
| ggg gcc gtg gtg gtg gac gtg gac ctg acg ccc gcg gca ccc agc agc<br>Gly Ala Val Val Val Asp Val Asp Leu Thr Pro Ala Ala Pro Ser Ser<br>                  195                       200                   205 | 804 |
| gag tcg ctg gcc ctg gac gaa gtg aca gcc atg gac aac cac gtg gca<br>Glu Ser Leu Ala Leu Asp Glu Val Thr Ala Met Asp Asn His Val Ala<br>         210                       215                   220 | 852 |
| ggg ctc ggg ccc gcg gag gag cgg cgt gcg ctg gtg ggt ccc ggc tct<br>Gly Leu Gly Pro Ala Glu Glu Arg Arg Ala Leu Val Gly Pro Gly Ser<br>225                       230                       235 | 900 |
| ccg ccc cgc agc gcg ccc ggc cag ctc cca tcg ccc cgg gcg cac agc<br>Pro Pro Arg Ser Ala Pro Gly Gln Leu Pro Ser Pro Arg Ala His Ser<br>240                       245                       250                   255 | 948 |
| ctc aac ccc gac gcc tcg ggc tcc agc tgc agc ctg gcc cgg acg cgc<br>Leu Asn Pro Asp Ala Ser Gly Ser Ser Cys Ser Leu Ala Arg Thr Arg<br>                  260                       265                   270 | 996 |
| tcc cga gaa agc tgc gcc agc gtg cgc cgc gcc tcg tcg gcc gac gac<br>Ser Arg Glu Ser Cys Ala Ser Val Arg Arg Ala Ser Ser Ala Asp Asp<br>               275                       280                   285 | 1044 |
| atc gag gcc atg cgc gcc ggg gtg ctg ccc ccg cca ccg cgc cac gcc<br>Ile Glu Ala Met Arg Ala Gly Val Leu Pro Pro Pro Pro Arg His Ala<br>         290                       295                   300 | 1092 |
| agc acc ggg gcc atg cac cca ctg cgc agc ggc ttg ctc aac tcc acc<br>Ser Thr Gly Ala Met His Pro Leu Arg Ser Gly Leu Leu Asn Ser Thr<br>305                       310                       315 | 1140 |
| tcg gac tcc gac ctc gtg cgc tac cgc acc att agc aag att ccc caa<br>Ser Asp Ser Asp Leu Val Arg Tyr Arg Thr Ile Ser Lys Ile Pro Gln<br>320                       325                       330                   335 | 1188 |
| atc acc ctc aac ttt gtg gac ctc aag ggc gac ccc ttc ttg gct tcg<br>Ile Thr Leu Asn Phe Val Asp Leu Lys Gly Asp Pro Phe Leu Ala Ser<br>               340                       345                   350 | 1236 |
| ccc acc agt gac cgt gag atc ata gca cct aag ata aag gag cga acc<br>Pro Thr Ser Asp Arg Glu Ile Ile Ala Pro Lys Ile Lys Glu Arg Thr<br>             355                       360                   365 | 1284 |
| cac aat gtc act gag aag gtc acc cag gtc ctg tcc ctg ggc gcc gac<br>His Asn Val Thr Glu Lys Val Thr Gln Val Leu Ser Leu Gly Ala Asp<br>         370                       375                   380 | 1332 |
| gtg ctg cct gag tac aag ctg cag gca ccg cgc atc cac cgc tgg acc<br>Val Leu Pro Glu Tyr Lys Leu Gln Ala Pro Arg Ile His Arg Trp Thr<br>385                       390                       395 | 1380 |
| atc ctg cat tac agc ccc ttc aag gcc gtg tgg gac tgg ctc atc ctg<br>Ile Leu His Tyr Ser Pro Phe Lys Ala Val Trp Asp Trp Leu Ile Leu<br>400                       405                       410                   415 | 1428 |

```
                                                           -continued
ctg ctg gtc atc tac acg gct gtc ttc aca ccc tac tcg gct gcc ttc    1476
Leu Leu Val Ile Tyr Thr Ala Val Phe Thr Pro Tyr Ser Ala Ala Phe
            420                 425                 430 ctg ctg aag gag acg gaa gaa ggc ccg cct gct acc gag tgt ggc tac    1524
Leu Leu Lys Glu Thr Glu Glu Gly Pro Pro Ala Thr Glu Cys Gly Tyr
            435                 440                 445 gcc tgc cag ccg ctg gct gtg gtg gac ctc atc gtg gac atc atg ttc    1572
Ala Cys Gln Pro Leu Ala Val Val Asp Leu Ile Val Asp Ile Met Phe
            450                 455                 460 att gtg gac atc ctc atc aac ttc cgc acc acc tac gtc aat gcc aac    1620
Ile Val Asp Ile Leu Ile Asn Phe Arg Thr Thr Tyr Val Asn Ala Asn
            465                 470                 475 gag gag gtg gtc agc cac ccc ggc cgc atc gcc gtc cac tac ttc aag    1668
Glu Glu Val Val Ser His Pro Gly Arg Ile Ala Val His Tyr Phe Lys
480                 485                 490                 495 ggc tgg ttc ctc atc gac atg gtg gcc gcc atc ccc ttc gac ctg ctc    1716
Gly Trp Phe Leu Ile Asp Met Val Ala Ala Ile Pro Phe Asp Leu Leu
                500                 505                 510 atc ttc ggc tct ggc tct gag gag ctg atc ggg ctg ctg aag act gcg    1764
Ile Phe Gly Ser Gly Ser Glu Glu Leu Ile Gly Leu Leu Lys Thr Ala
                515                 520                 525 cgg ctg ctg cgg ctg gtg cgc gtg gcg cgg aag ctg gat cgc tac tca    1812
Arg Leu Leu Arg Leu Val Arg Val Ala Arg Lys Leu Asp Arg Tyr Ser
            530                 535                 540 gag tac ggc gcg gcc gtg ctg ttc ttg ctc atg tgc acc ttt gcg ctc    1860
Glu Tyr Gly Ala Ala Val Leu Phe Leu Leu Met Cys Thr Phe Ala Leu
            545                 550                 555 atc gcg cac tgg cta gcc tgc atc tgg tac gcc atc ggc aac atg gag    1908
Ile Ala His Trp Leu Ala Cys Ile Trp Tyr Ala Ile Gly Asn Met Glu
560                 565                 570                 575 cag cca cac atg gac tca cgc atc ggc tgg ctg cac aac ctg ggc gac    1956
Gln Pro His Met Asp Ser Arg Ile Gly Trp Leu His Asn Leu Gly Asp
                580                 585                 590 cag ata ggc aaa ccc tac aac agc agc ggc ctg ggc ggc ccc tcc atc    2004
Gln Ile Gly Lys Pro Tyr Asn Ser Ser Gly Leu Gly Gly Pro Ser Ile
                595                 600                 605 aag gac aag tat gtg acg gcg ctc tac ttc acc ttc agc agc ctc acc    2052
Lys Asp Lys Tyr Val Thr Ala Leu Tyr Phe Thr Phe Ser Ser Leu Thr
            610                 615                 620 agt gtg ggc ttc ggc aac gtc tct ccc aac acc aac tca gag aag atc    2100
Ser Val Gly Phe Gly Asn Val Ser Pro Asn Thr Asn Ser Glu Lys Ile
625                 630                 635 ttc tcc atc tgc gtc atg ctc att ggc tcc ctc atg tat gct agc atc    2148
Phe Ser Ile Cys Val Met Leu Ile Gly Ser Leu Met Tyr Ala Ser Ile
640                 645                 650                 655 ttc ggc aac gtg tcg gcc atc atc cag cgg ctg tac tcg ggc aca gcc    2196
Phe Gly Asn Val Ser Ala Ile Ile Gln Arg Leu Tyr Ser Gly Thr Ala
                660                 665                 670 cgc tac cac aca cag atg ctg cgg gtg cgg gag ttc atc cgc ttc cac    2244
Arg Tyr His Thr Gln Met Leu Arg Val Arg Glu Phe Ile Arg Phe His
            675                 680                 685 cag atc ccc aat ccc ctg cgc cag cgc ctc gag gag tac ttc cag cac    2292
Gln Ile Pro Asn Pro Leu Arg Gln Arg Leu Glu Glu Tyr Phe Gln His
            690                 695                 700 gcc tgg tcc tac acc aac ggc atc gac atg aac gcg gtg ctg aag ggc    2340
Ala Trp Ser Tyr Thr Asn Gly Ile Asp Met Asn Ala Val Leu Lys Gly
705                 710                 715 ttc cct gag tgc ctg cag gct gac atc tgc ctg cac ctg aac cgc tca    2388
Phe Pro Glu Cys Leu Gln Ala Asp Ile Cys Leu His Leu Asn Arg Ser
720                 725                 730                 735
```

```
ctg ctg cag cac tgc aaa ccc ttc cga ggg gcc acc aag ggc tgc ctt    2436
Leu Leu Gln His Cys Lys Pro Phe Arg Gly Ala Thr Lys Gly Cys Leu
            740                 745                 750 cgg gcc ctg gcc atg aag ttc aag acc aca cat gca ccg cca ggg gac    2484
Arg Ala Leu Ala Met Lys Phe Lys Thr Thr His Ala Pro Pro Gly Asp
        755                 760                 765 aca ctg gtg cat gct ggg gac ctg ctc acc gcc ctg tac ttc atc tcc    2532
Thr Leu Val His Ala Gly Asp Leu Leu Thr Ala Leu Tyr Phe Ile Ser
        770                 775                 780 cgg ggc tcc atc gag atc ctg cgg ggc gac gtc gtc gtg gcc atc ctg    2580
Arg Gly Ser Ile Glu Ile Leu Arg Gly Asp Val Val Val Ala Ile Leu
        785                 790                 795 ggg aag aat gac atc ttt ggg gag cct ctg aac ctg tat gca agg cct    2628
Gly Lys Asn Asp Ile Phe Gly Glu Pro Leu Asn Leu Tyr Ala Arg Pro
800                 805                 810                 815 ggc aag tcg aac ggg gat gtg cgg gcc ctc acc tac tgt gac cta cac    2676
Gly Lys Ser Asn Gly Asp Val Arg Ala Leu Thr Tyr Cys Asp Leu His
                820                 825                 830 aag atc cat cgg gac gac ctg ctg gag gtg ctg gac atg tac cct gag    2724
Lys Ile His Arg Asp Asp Leu Leu Glu Val Leu Asp Met Tyr Pro Glu
            835                 840                 845 ttc tcc gac cac ttc tgg tcc agc ctg gag atc acc ttc aac ctg cga    2772
Phe Ser Asp His Phe Trp Ser Ser Leu Glu Ile Thr Phe Asn Leu Arg
        850                 855                 860 gat acc aac atg atc ccg ggc tcc ccc ggc agt acg gag tta gag ggt    2820
Asp Thr Asn Met Ile Pro Gly Ser Pro Gly Ser Thr Glu Leu Glu Gly
        865                 870                 875 ggc ttc agt cgg caa cgc aag cgc aag ttg tcc ttc cgc agg cgc acg    2868
Gly Phe Ser Arg Gln Arg Lys Arg Lys Leu Ser Phe Arg Arg Arg Thr
880                 885                 890                 895 gac aag gac acg gag cag cca ggg gag gtg tcg gcc ttg ggg ccg ggc    2916
Asp Lys Asp Thr Glu Gln Pro Gly Glu Val Ser Ala Leu Gly Pro Gly
                900                 905                 910 cgg gcg ggg gca ggg ccg agt agc cgg ggc cgg ccg ggg ggg ccg tgg    2964
Arg Ala Gly Ala Gly Pro Ser Ser Arg Gly Arg Pro Gly Gly Pro Trp
            915                 920                 925 ggg gag agc ccg tcc agt ggc ccc tcc agc cct gag agc agt gag gat    3012
Gly Glu Ser Pro Ser Ser Gly Pro Ser Ser Pro Glu Ser Ser Glu Asp
        930                 935                 940 gag ggc cca ggc cgc agc tcc agc ccc ctc cgc ctg gtg ccc ttc tcc    3060
Glu Gly Pro Gly Arg Ser Ser Ser Pro Leu Arg Leu Val Pro Phe Ser
        945                 950                 955 agc ccc agg ccc ccc gga gag ccg ccg gtg ggg gag ccc ctg atg gag    3108
Ser Pro Arg Pro Pro Gly Glu Pro Pro Gly Gly Glu Pro Leu Met Glu
960                 965                 970                 975 gac tgc gag aag agc agc gac act tgc aac ccc ctg tca ggc gcc ttc    3156
Asp Cys Glu Lys Ser Ser Asp Thr Cys Asn Pro Leu Ser Gly Ala Phe
                980                 985                 990 tca gga gtg tcc aac att ttc agc ttc tgg ggg gac agt cgg ggc cgc    3204
Ser Gly Val Ser Asn Ile Phe Ser Phe Trp Gly Asp Ser Arg Gly Arg
            995                 1000                1005 cag tac cag gag ctc cct cga tgc ccc gcc ccc acc ccc agc ctc        3249
Gln Tyr Gln Glu Leu Pro Arg Cys Pro Ala Pro Thr Pro Ser Leu
        1010                1015                1020 ctc aac atc ccc ctc tcc agc ccg ggt cgg cgg ccc cgg ggc gac        3294
Leu Asn Ile Pro Leu Ser Ser Pro Gly Arg Arg Pro Arg Gly Asp
        1025                1030                1035 gtg gag agc agg ctg gat gcc ctc cag cgc cag ctc aac agg ctg        3339
Val Glu Ser Arg Leu Asp Ala Leu Gln Arg Gln Leu Asn Arg Leu
        1040                1045                1050
```

```
gag acc cgg ctg agt gca gac atg gcc act gtc ctg cag ctg cta    3384
Glu Thr Arg Leu Ser Ala Asp Met Ala Thr Val Leu Gln Leu Leu
        1055                1060                1065 cag agg cag atg acg ctg gtc ccg ccc gcc tac agt gct gtg acc    3429
Gln Arg Gln Met Thr Leu Val Pro Pro Ala Tyr Ser Ala Val Thr
        1070                1075                1080 acc ccg ggg cct ggc ccc act tcc aca tcc ccg ctg ttg ccc gtc    3474
Thr Pro Gly Pro Gly Pro Thr Ser Thr Ser Pro Leu Leu Pro Val
        1085                1090                1095 agc ccc ctc ccc acc ctc acc ttg gac tcg ctt tct cag gtt tcc    3519
Ser Pro Leu Pro Thr Leu Thr Leu Asp Ser Leu Ser Gln Val Ser
        1100                1105                1110 cag ttc atg gcg tgt gag gag ctg ccc ccg ggg gcc cca gag ctt    3564
Gln Phe Met Ala Cys Glu Glu Leu Pro Pro Gly Ala Pro Glu Leu
        1115                1120                1125 ccc caa gaa ggc ccc aca cga cgc ctc tcc cta ccg ggc cag ctg    3609
Pro Gln Glu Gly Pro Thr Arg Arg Leu Ser Leu Pro Gly Gln Leu
        1130                1135                1140 ggg gcc ctc acc tcc cag ccc ctg cac aga cac ggc tcg gac ccg    3654
Gly Ala Leu Thr Ser Gln Pro Leu His Arg His Gly Ser Asp Pro
        1145                1150                1155 ggc agt tagtgggget gcccagtgtg acacgtggc tcacccaggg atcaaggcgc   3710
Gly Ser tgctgggccg ctcccttgg aggccctgct caggaggccc tgaccgtgga agggagagg   3770 aactcgaaag cacagctcct cccccagccc ttgggaccat cttctcctgc agtccctgg   3830 gccccagtga gggggcagg ggcagggccg gcagtaggtg gggcctgtgg tcccccact   3890 gccctgaggg cattagctgg tctaactgcc cggaggcacc cggccctggg ccttaggcac   3950
ctcaaggact tttctgctat ttactgctct tattgttaag gataataatt aaggatcata   4010
tgaataatta atgaagatgc tgatgactat gaataataaa taattatcct gaggagaaaa   4070

<210> SEQ ID NO 2
<211> LENGTH: 1159
<212> TYPE: PRT
<213> ORGANISM: Homo Sapiens

<400> SEQUENCE: 2

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
    130                 135                 140

Thr Asn His Arg Gly Pro Pro Thr Ser Trp Leu Ala Pro Gly Arg Ala
145                 150                 155                 160
```

```
Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
            245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
            405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
        435                 440                 445

Cys Gln Pro Leu Ala Val Val Asp Leu Ile Val Asp Ile Met Phe Ile
    450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
            485                 490                 495

Trp Phe Leu Ile Asp Met Val Ala Ala Ile Pro Phe Asp Leu Leu Ile
            500                 505                 510

Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
    530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
            565                 570                 575

Pro His Met Asp Ser Arg Ile Gly Trp Leu His Asn Leu Gly Asp Gln
```

```
                580             585             590
Ile Gly Lys Pro Tyr Asn Ser Ser Gly Leu Gly Gly Pro Ser Ile Lys
            595                 600             605

Asp Lys Tyr Val Thr Ala Leu Tyr Phe Thr Phe Ser Ser Leu Thr Ser
            610                 615             620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
                660                 665                 670

Tyr His Thr Gln Met Leu Arg Val Arg Glu Phe Ile Arg Phe His Gln
                675                 680                 685

Ile Pro Asn Pro Leu Arg Gln Arg Leu Glu Glu Tyr Phe Gln His Ala
            690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
                740                 745                 750

Ala Leu Ala Met Lys Phe Lys Thr Thr His Ala Pro Pro Gly Asp Thr
                755                 760                 765

Leu Val His Ala Gly Asp Leu Leu Thr Ala Leu Tyr Phe Ile Ser Arg
            770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
                835                 840                 845

Ser Asp His Phe Trp Ser Ser Leu Glu Ile Thr Phe Asn Leu Arg Asp
            850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Arg Thr Asp
                885                 890                 895

Lys Asp Thr Glu Gln Pro Gly Glu Val Ser Ala Leu Gly Pro Gly Arg
                900                 905                 910

Ala Gly Ala Gly Pro Ser Ser Arg Gly Arg Pro Gly Gly Pro Trp Gly
            915                 920                 925

Glu Ser Pro Ser Ser Gly Pro Ser Ser Pro Glu Ser Ser Glu Asp Glu
            930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg  Gly Arg Gln
            995                 1000                1005
```

-continued

```
Tyr Gln Glu Leu Pro Arg Cys Pro Ala Pro Thr Pro Ser Leu Leu
    1010            1015                1020
Asn Ile Pro Leu Ser Ser Pro Gly Arg Arg Pro Arg Gly Asp Val
    1025            1030                1035
Glu Ser Arg Leu Asp Ala Leu Gln Arg Gln Leu Asn Arg Leu Glu
    1040            1045                1050
Thr Arg Leu Ser Ala Asp Met Ala Thr Val Leu Gln Leu Leu Gln
    1055            1060                1065
Arg Gln Met Thr Leu Val Pro Pro Ala Tyr Ser Ala Val Thr Thr
    1070            1075                1080
Pro Gly Pro Gly Pro Thr Ser Thr Ser Pro Leu Leu Pro Val Ser
    1085            1090                1095
Pro Leu Pro Thr Leu Thr Leu Asp Ser Leu Ser Gln Val Ser Gln
    1100            1105                1110
Phe Met Ala Cys Glu Glu Leu Pro Pro Gly Ala Pro Glu Leu Pro
    1115            1120                1125
Gln Glu Gly Pro Thr Arg Arg Leu Ser Leu Pro Gly Gln Leu Gly
    1130            1135                1140
Ala Leu Thr Ser Gln Pro Leu His Arg His Gly Ser Asp Pro Gly
    1145            1150                1155
Ser

<210> SEQ ID NO 3
<211> LENGTH: 31
<212> TYPE: DNA
<213> ORGANISM: Artificial
<220> FEATURE:
<223> OTHER INFORMATION: primer

<400> SEQUENCE: 3
aattggtacc atgggctcag gatgccggtg c                             31

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
gcttgtactc aggcagcacg t                                        21

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
ccaccagtga ccgtgagatc a                                        21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ttgcagtgct gcagcagtga g                                        21
```

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
atgctagcat cttcggcaac g                                              21

<210> SEQ ID NO 8
<211> LENGTH: 31
<212> TYPE: DNA
<213> ORGANISM: Artificial
<220> FEATURE:
<223> OTHER INFORMATION: primer

<400> SEQUENCE: 8
aattaagctt tttcgagttc ctctcccctt c                                   31

<210> SEQ ID NO 9
<211> LENGTH: 52
<212> TYPE: DNA
<213> ORGANISM: Artificial
<220> FEATURE:
<223> OTHER INFORMATION: oligo DNA

<400> SEQUENCE: 9
gatcccccgg gctgcaggaa ttcgatatcg ttaacgtcga cctcgagggt ac            52

<210> SEQ ID NO 10
<211> LENGTH: 44
<212> TYPE: DNA
<213> ORGANISM: Artificial
<220> FEATURE:
<223> OTHER INFORMATION: oligo DNA

<400> SEQUENCE: 10
cctcgaggtc gacgttaacg atatcgaatt cctgcagccc gggg                     44

<210> SEQ ID NO 11
<211> LENGTH: 32
<212> TYPE: DNA
<213> ORGANISM: Artificial
<220> FEATURE:
<223> OTHER INFORMATION: primer

<400> SEQUENCE: 11
gtcgtcatcg atacaaatgg cagtattcat cc                                  32

<210> SEQ ID NO 12
<211> LENGTH: 34
<212> TYPE: DNA
<213> ORGANISM: Artificial
<220> FEATURE:
<223> OTHER INFORMATION: primer

<400> SEQUENCE: 12
gtcgtcaagc ttccaaactg gatctctgct gtcc                                34

<210> SEQ ID NO 13
<211> LENGTH: 5020
<212> TYPE: DNA
<213> ORGANISM: Retroviral provirus

<400> SEQUENCE: 13

```
ctgcagcctg aatatgggcc aaacaggata tctgtggtaa gcagttcctg ccccggctca    60
gggccaagaa cagatggaac agctgaatat gggccaaaca ggatatctgt ggtaagcagt   120
tcctgccccg gctcagggcc aagaacagat ggtccccaga tgcggtccag ccctcagcag   180
tttctagaga accatcagat gtttccaggg tgccccaagg acctgaaatg accctgtgcc   240
ttatttgaac taaccaatca gttcgcttct cgcttctgtt cgcgcgcttc tgctccccga   300
gctcaataaa agagcccaca acccctcact cggggcgcca gtcctccgat tgactgagtc   360
gcccgggtac ccgtgtatcc aataaaccct cttgcagttg catccgactt gtggtctcgc   420
tgttccttgg gagggtctcc tctgagtgat tgactacccg tcagcggggg tctttcattt   480
gggggctcgt ccgggatcgg gagacccctg cccagggacc accgacccac caccgggagg   540
taagctggcc agcaacttat ctgtgtctgt ccgattgtct agtgtctatg actgatttta   600
tgcgcctgcg tcggtactag ttagctaact agctctgtat ctggcggacc cgtggtggaa   660
ctgacgagtt ctgaacaccc ggccgcaacc ctgggagacg tcccaggac  tttggggcc    720
gttttttgtgg cccgacctga ggaagggagt cgatgtggaa tccgaccccg tcaggatatg   780
tggttctggt aggagacgag aacctaaaac agttcccgcc tccgtctgaa ttttttgcttt   840
cggtttggaa ccgaagccgc gcgtcttgtc tgctgcagca tcgttctgtg ttgtctctgt   900
ctgactgtgt ttctgtattt gtctgaaaat tagggccaga ctgttaccac tcccttaagt   960
ttgaccttag atcactggaa agatgtcgag cggctcgctc acaaccagtc ggtagatgtc  1020
aagaagagac gttgggttac cttctgctct gcagaatggc caacctttaa cgtcggatgg  1080
ccgcgagacg gcacctttaa ccgagacctc atcacccagg ttaagatcaa ggtctttca   1140
cctggcccgc atggacaccc agaccaggtc ccctacatcg tgacctggga agccttggct  1200
tttgaccccc ctccctgggt caagcccttt gtacacccta agcctccgcc tcctcttctt  1260
ccatccgcgc cgtctctccc ccttgaacct cctctttcga cccgcctca  atcctccctt  1320
tatccagccc tcactccttc tctaggcgcc ggccggatcc cagtgtggtg gtacgtagga  1380
attcgccagc acagtggtcg acctgtggaa tgtgtgtcag ttagggtgtg aaagtcccc   1440
aggctcccca gcaggcagaa gtatgcaaag catgcatctc aattagtcag caaccaggtg  1500
tggaaagtcc ccaggctccc cagcaggcag aagtatgcaa agcatgcatc tcaattagtc  1560
agcaaccata gtcccgcccc taactccgcc catcccgccc ctaactccgc ccagttccgc  1620
ccattctccg ccccatggct gactaatttt ttttatttat gcagaggccg aggccgcctc  1680
ggcctctgag ctattccaga agtagtgagg aggcttttt  ggaggcctag cttttgcaa   1740
acgctgcttg aggctgaagg tgcgttgctg gcgttttcc  ataggctccg ccccctgac   1800
gagcatcaca aaaatcgacg ctcaagtcag aggtggcgaa acccgacagg actataaaga  1860
taccaggcgt ttccccctgg aagctccctc gtgcgctctc ctgttccgac cctgccgctt  1920
accggatacc tgtccgcctt tctcccttcg ggaagcgtgg cgctttctca tagctcacgc  1980
tgtaggtatc tcagttcggt gtaggtcgtt cgctccaagc tgggctgtgt gcacgaaccc  2040
cccgttcagc ccgaccgctg cgccttatcc ggtaactatc gtcttgagtc aacccggta   2100
agacacgact tatcgccact ggcagcagcc actggtaaca ggattagcag agcgaggtat  2160
gtaggcggtg ctacagagtt cttgaagtgg tggcctaact acggctacac tagaaggaca  2220
gtatttggta tctgcgctct gctgaagcca gttaccttcg gaaaaagagt tggtagctct  2280
tgatccggca acaaaccac  cgctggtagc ggtggttttt ttgtttgcaa gcagcagatt  2340
acgatcgata aaataaaaga tttttatttag tctccagaaa aagggggga  tgaaagaccc  2400
```

```
cacctgtagg tttggcaagc tagcttaagt aacgccattt tgcaaggcat ggaaaaatac    2460
ataactgaga atagagaagt tcagatcaag gtcaggaaca gatggaacag ctgaatatgg    2520
gccaaacagg atatctgtgg taagcagttc ctgccccggc tcagggccaa gaacagatgg    2580
aacagctgaa tatgggccaa acaggatatc tgtggtaagc agttcctgcc ccggctcagg    2640
gccaagaaca gatggtcccc agatgcggtc cagccctcag cagtttctag agaaccatca    2700
gatgttttcca gggtgcccca aggacctgaa atgaccctgt gccttatttg aactaaccaa    2760
tcagttcgct tctcgcttct gttcgcgcgc ttctgctccc cgagctcaat aaaagagccc    2820
acaacccctc actcggggcg ccagtcctcc gattgactga gtcgcccggg tacccgtgta    2880
tccaataaac cctcttgcag ttgcatccga cttgtggtct cgctgttcct gggagggtc    2940
tcctctgagt gattgactac ccgtcagcgg gggtctttca catgcagcat gtatcaaaat    3000
taatttggtt ttttttctta agtatttaca ttaaatggcc atagttgcat taatgaatcg    3060
gccaacgcgc ggggagaggc ggtttgcgta ttgggcgctc ttccgcttcc tcgctcactg    3120
actcgctgcg ctcggtcgtt cggctgcggc gagcggtatc agctcactca aaggcggtaa    3180
tacggttatc cacagaatca ggggataacg caggaaagaa catgtgagca aaaggccagc    3240
aaaaggccag gaaccgtaaa aaggccgcgt tgctggcgtt tttccatagg ctccgccccc    3300
ctgacgagca tcacaaaaat cgacgctcaa gtcagaggtg cgaaacccg acaggactat    3360
aaagatacca ggcgtttccc cctggaagct ccctcgtgcg ctctcctgtt ccgaccctgc    3420
cgcttaccgg atacctgtcc gcctttctcc cttcgggaag cgtggcgctt tctcatagct    3480
cacgctgtag gtatctcagt tcggtgtagg tcgttcgctc caagctgggc tgtgtgcacg    3540
aaccccccgt tcagcccgac cgctgcgcct tatccggtaa ctatcgtctt gagtccaacc    3600
cggtaagaca cgacttatcg ccactggcag cagccactgg taacaggatt agcagagcga    3660
ggtatgtagg cggtgctaca gagttcttga agtggtggcc taactacggc tacactagaa    3720
ggacagtatt tggtatctgc gctctgctga agccagttac cttcggaaaa agagttggta    3780
gctcttgatc cggcaaacaa accaccgctg gtagcggtgg ttttttttgtt tgcaagcagc    3840
agattacgcg cagaaaaaaa ggatctcaag aagatccttt gatcttttct acggggtctg    3900
acgctcagtg gaacgaaaac tcacgttaag ggattttggt catgagatta tcaaaaagga    3960
tcttcaccta gatccttttaa aattaaaaat gaagtttgcg ccgcaaatc aatctaaagt    4020
atatatgagt aaacttggtc tgacagttac caatgcttaa tcagtgaggc acctatctca    4080
gcgatctgtc tatttcgttc atccatagtt gcctgactcc ccgtcgtgta gataactacg    4140
atacgggagg gcttaccatc tggccccagt gctgcaatga taccgcgaga cccacgctca    4200
ccggctccag atttatcagc aataaaccag ccagccggaa gggccgagcg cagaagtggt    4260
cctgcaactt tatccgcctc catccagtct attaattgtt gccgggaagc tagagtaagt    4320
agttcgccag ttaatagttt gcgcaacgtt gttgccattg ctacaggcat cgtggtgtca    4380
cgctcgtcgt ttggtatggc ttcattcagc tccggttccc aacgatcaag gcgagttaca    4440
tgatccccca tgttgtgcaa aaaagcggtt agctccttcg gtcctccgat cgttgtcaga    4500
agtaagttgg ccgcagtgtt atcactcatg gttatggcag cactgcataa ttctcttact    4560
gtcatgccat ccgtaagatg cttttctgtg actggtgagt actcaaccaa gtcattctga    4620
gaatagtgta tgcggcgacc gagttgctct tgcccggcgt caacacggga taataccgcg    4680
ccacatagca gaactttaaa agtgctcatc attggaaaac gttcttcggg gcgaaaactc    4740
tcaaggatct taccgctgtt gagatccagt tcgatgtaac ccactcgtgc acccaactga    4800
```

| | | | | | |
|---|---|---|---|---|---|
| tcttcagcat | cttttacttt | caccagcgtt | tctgggtgag | caaaaacagg | aaggcaaaat | 4860
| gccgcaaaaa | agggaataag | ggcgacacgg | aaatgttgaa | tactcatact | cttccttttt | 4920
| caatattatt | gaagcattta | tcagggttat | tgtctcatga | gcggatacat | atttgaatgt | 4980
| atttagaaaa | ataaacaaat | aggggttccg | cgcacatttc | | | 5020

HERG CHANNEL-EXPRESSING CELL

CROSS REFERENCE TO PRIOR RELATED APPLICATIONS

This application is a U.S. national phase application under 35 U.S.C. §371 of International Patent Application No. PCT/JP2004/017441, filed Nov. 17, 2004 and claims the benefit of Japanese Patent Application No. 2003-387255, filed Nov. 17, 2003, both of which are incorporated by reference herein. The International Application was published in Japanese on May 26, 2005 as International Publication No. WO 2005/047500 A1 under PCT Article 21(2).

TECHNICAL FIELD

The present invention relates to cells for evaluation in order to avoid the risk of adverse effects on the heart caused by electrocardiographic QT interval prolongation which is a big safety problem in research and development of drugs, as well as methods for establishing such cells and evaluation of drugs using the established cells.

BACKGROUND ART

Safety pharmacological studies are non-clinical studies to examine the safety of novel drugs on human from pharmacological viewpoints. Guideline on Safety Pharmacology Studies which aims at examining the safety of test substances on human and predicting adverse effects thereof has been set in the International Conference on Harmonisation of Technical Requirements for Registration of Pharmaceuticals for Human Use (ICH) between Europe, Japan and the United States. According to the Guideline, examination of the arrhythmogenic effect, in particular, the presence or absence of electrocardiographic QT interval prolongation effect, of test substances is required as a part of safety pharmacological studies. In order to protect patients from ventricular tachycardia, torsades de pointes and lethal arrhythmia associated with QT interval prolongation induced by drug administration, it is very important in the development of drugs to detect QT interval prolongation effect which may induce such serious adverse effects.

To date, it has been known that a large number of drugs having QT interval prolongation effect inhibit delayed rectifier potassium channels in cardiomyocytes. It is believed that hERG (human ether-a-go-go related gene) channel is functioning as a major constituent protein in the delayed rectifier potassium channel. Therefore, in the draft guideline for non-clinical evaluation of the potential for delayed ventricular repolarization (QT Interval Prolongation) by human pharmaceuticals (ICH-S7B), ion channel assay using hERG channel-transferred cells is recommended as a non-clinical study.

Conventionally, as a method of appropriately evaluating the effect of a compound on hERG channels, the patch clamp technique has been used in which channel activities of cells that had been allowed to express hERG channels or cardiomyocytes inherently possessing hERG channels are recorded by direct use of glass microelectrodes to the cells or cardiomyocytes (Neher, E. and Sakmann, B., Nature, Vol 260, 779-802, (1976)). However, though this patch clamp technique enables appropriate evaluation of drugs on hERG channels with high accuracy, it has the following problems. That is, it requires highly skilled technology, has a remarkably low throughput (1-5 compounds/day/person) and thus is remarkably insufficient in throughput for a great number of candidate compounds at the development stage of drugs.

On the other hand, as methods for enhancing the throughput of hERG channel evaluation, a method of detecting the release of a radioactive isotope $Rb^{3+}$ (Cheng, C. S. et al., Drug Dev. Ind. Pharm. vol. 28, 177-191, (2002)), a method in which competitive binding to a radioactive isotope tritium ($^3H$)-labeled dofetilide is observed and evaluated (Finlayson, K. et al. Eur. J. Pharm. vol. 430, 147-148 (2001)) and a method using membrane potential sensitive dyes (Tang, W et al. J. Biomol. Screen vol. 6, 325-331 (2001); Baxter, D. F. et al. ibid. vol. 7, 79-85 (2003)) have been reported. However, these methods are complicated in operations because radioactive substances are used. Besides, since they are indirect methods, their sensitivity and accuracy are low and far from the measurement accuracy that can be obtained by the patch clamp technique.

Recently, fully automated high throughput patch clamp systems which evaluate the influence by hERG channels appropriately and at the same time have a high throughput have been developed as means to solve the above-described problems. Some of such instruments have been commercialized (IonWorks HT™ from Molecular Device; PatchXpress™ 7000A from Axon Instruments). These apparatuses are intended to suspend hERG channel-expressing cells, suck the cells into a small hole located at the center of each well utilizing dropping by gravity and negative pressure, and to thereby make the cells capable of current recording. Therefore, the highly skilled technology required in the patch clamp technique is not necessary. Besides, the throughput of compounds is very high; data from more than 3000 points can be obtained per day. However, for making evaluation with such an apparatus, hERG channel-expressing cells used in experiments are extremely important. While it is possible to select hERG channel high expressing cells for measuring in the conventional patch clamp technique where a single cell is selected and evaluated, it is impossible to select high expressing cells in measurement with a fully automated high throughput patch clamp system because cells present are used at random. Therefore, in order to evaluate multiple samples accurately with a fully automated high throughput patch clamp system, more than a specific ratio of cells must be expressing hERG channels and yet the expression levels must be sufficient. Various attempts have been made to prepare hERG channel-expressing cells which can be used in this fully automated high throughput patch clamp system.

According to reports so far made, stably expressing cells were obtained by introducing hERG gene into cells by transfection using the calcium phosphate method or lipofection and then performing extremely labor-consuming procedures such as cloning cells by the limiting dilution culture method and confirming the quantity of transferred hERG gene, or measurement of currents through hERG channels (Tang, W. et al. J. Biomol. Screen, vol. 6 325-331 (2001); Assay and Drug Development Technologies, 1(2-3), 127-135, 2003). However, these techniques cannot secure a sufficient quantity of transferred hERG gene even by spending a great labor of cloning by the limiting dilution culture method, which results in a very weak hERG current per cell. When the hERG current is small, it is impossible to obtain a sufficient S/N ratio and, as a result, measurement sensitivity decreases. Further, even when a cell with whatever large hERG current has been obtained by cloning, it is often difficult to measure the amplitude of the hERG current with high sensitivity with a fully automated high throughput patch clamp system.

In measurement of currents in the ion channel into which hERG channel is classified, influence of the ion channel which cells endogenously have varies by cell species. Therefore, the practical value of measurement often varies greatly by changing cell species. For this reason, it was also necessary to repeat labor-consuming operations such as described above when measurement was performed with a different cell species.

DISCLOSURE OF THE INVENTION

The present invention has been made under such circumstances. It is an object of the present invention to establish a method of establishing a cell with a remarkably high hERG channel expression level for use in predicting adverse effects based on hERG channel inhibition in research and development of drugs, and to thereby establish a highly sensitive and high throughput evaluation method for test substances.

As a result of extensive and intensive researches toward the solution of the above-described problems, the present inventors have succeeded in obtaining a hERG channel high expressing cell by inserting a hERG gene into a retrovirus vector plasmid or lentivirus vector plasmid to thereby prepare a virus vector, concentrating the vector by ultracentrifugation if necessary, and transferring the hERG gene into cells. The inventors have also found that, with the resultant cell, it is possible to secure an expression level effective in measurement using a fully automated high throughput patch clamp system or dyes. Thus, the present invention has been achieved.

The present invention has such aspects as:
A hERG channel-expressing cell population containing cells capable of expressing a channel of which the hERG current as determined by patch clamping with a fully automated high throughput patch clamp system is 0.6 nA or more, wherein the ratio of the cells is 40% or more relative to the total number of hERG gene-transferred cells within the population;
The cell population according to the above aspect wherein the hERG gene has been transferred with a virus vector;
The cell population according to the above aspect, wherein the virus vector is a retrovirus vector or a lentivirus vector;
The cell population according to any one of the aspects above, wherein the average value of hERG current in the total cells is 0.3 nA or more;
A cell capable of expressing a hERG channel of which the hERG current as determined by patch clamping with a fully automated high throughput patch clamp system is 1.0 nA or more;
The cell according to the above aspect wherein the hERG gene has been transferred with a virus vector;
The cell according to the above aspect, wherein the virus vector is a retrovirus vector or a lentivirus vector;
A method of preparing the cell population or the cell according to any one of the aspects above, which includes expressing hERG channels using a virus vector;
The method according to the above aspect, wherein the virus vector is a retrovirus vector or a lentivirus vector;
The method according to the above aspect wherein the virus vector is a retrovirus vector;
The method according to one of the aspects above, which includes a step of concentrating the virus vector by ultracentrifugation;
A method of measuring hERG current inhibitory activity, which includes using the cell population or the cell according to one of the aspects above;
The method according to the above aspect which includes using a fully automated high throughput patch clamp system;
A method of measuring hERG current inhibitory activity, which includes using a cell population or a cell prepared by the method according to one of the aspects above;
The method according to the above aspect, which includes using a fully automated high throughput patch clamp system;
A method of screening for compounds, or salts thereof, that alter or do not alter hERG currents, which includes using the cell population or the cell according to one of the aspects above;
The method according to the above aspect, which includes using a fully automated high throughput patch clamp system;
A method of screening for compounds, or salts thereof, that alter or do not alter hERG currents, which includes using a cell population or a cell prepared by the method according to one of the aspects above; and
The method according to the above aspect, which includes using a fully automated high throughput patch clamp system.

According to the present invention, a method of establishing a cell with a remarkably high hERG channel expression level for use in predicting adverse effects based on hERG channel inhibition in research and development of drugs has been established; with that method, highly sensitive and high throughput evaluation has become possible.

Further, according to the present invention, hERG channel high expressing cells can be obtained simultaneously and efficiently. With this advantage, by allowing a wide variety of cell species to express hERG channel at high levels and comparing influences of endogenous ion channels among those cell species, it has become possible to select the most suitable cell species for predicting adverse effects in research and development of drugs. Further, the hERG channel-expressing cell or hERG channel-expressing cell population of the present invention is capable of expressing hERG channels stably for a long period of time.

BEST MODE FOR CARRYING OUT THE INVENTION

Figure 1:
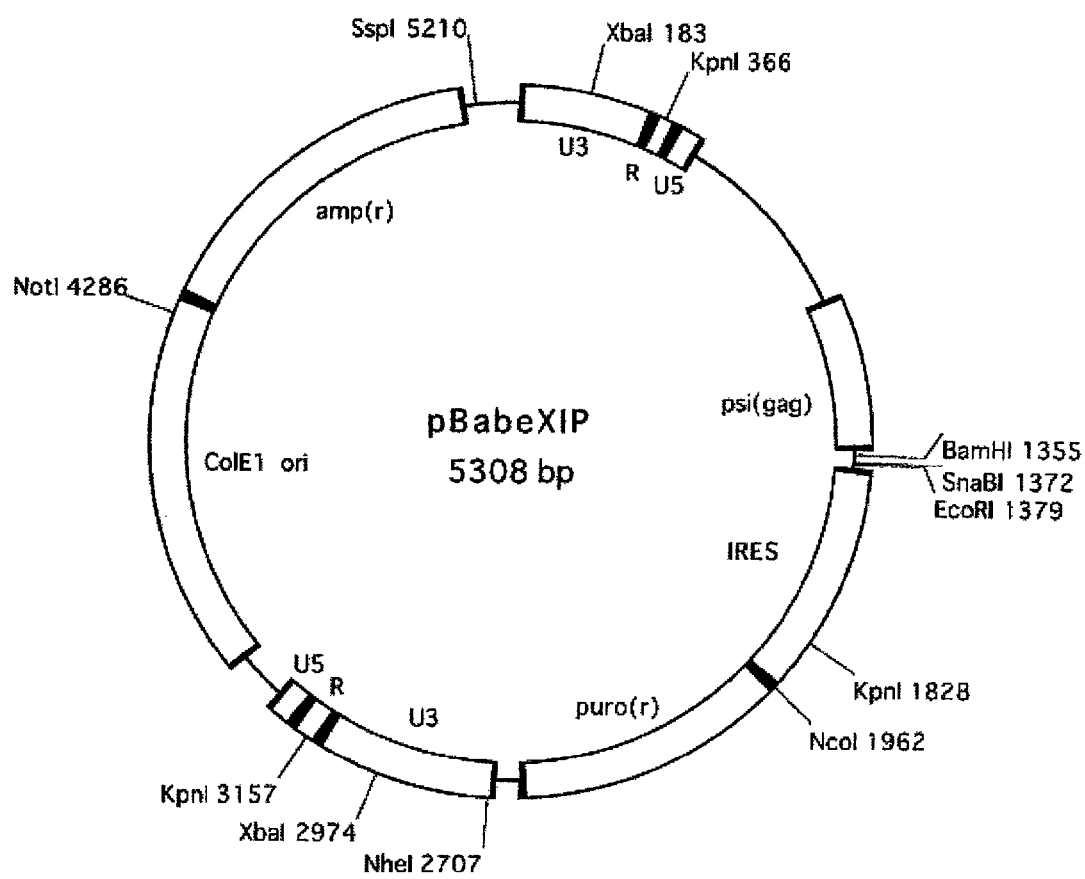
FIG. 1 shows the structure of a retrovirus vector plasmid (pBabeXIP).

Hereinbelow, embodiments of the present invention will be described. The following embodiments are provided only for the purpose of illustration of the present invention. It is not intended to limit the present invention to the following embodiments. The present invention can be practiced in various other embodiments without departing from the spirit of the invention.

In the present invention, it is possible to prepare a hERG gene-containing virus vector using a retrovirus or lentivirus vector plasmid and to allow cells to express hERG channels at high levels using the resultant virus vector. In the present invention, it is also possible to identify substances that inhibit hERG currents by using the hERG channel-expressing cell or cell population obtained by the present invention in measuring methods with a fully automated high throughput patch clamp system or a dye. Besides, the hERG channel-expressing cell or hERG channel-expressing cell population of the present invention is capable of expressing hERG channels stably for a long period of time.

In the present invention, the "patch clamp technique" or "patch clamping" refers to a technique to detect ionic flows passing through ion channels present on cell membranes with high sensitivity ("New Patch Clamp Experiment Technique", Yasunobu Okada Ed., Yoshioka Shoten). In the present invention, the term "conventional patch clamp technique" or "conventional patch clamping" refers to the whole cell patch clamp technique in which a highly skilled researcher presses glass microelectrodes 0.5-3 µm in diameter against a cell under microscopic observation to create a high resistant state and then destroys the relevant patch to thereby record currents passing through the ion channels present on the cell membrane surface.

In the present invention, the "patch clamp technique (or patch clamping) with a fully automated high throughput patch clamp system" refers to the perforated whole cell patch clamp technique where: cells are set in a measuring apparatus in a state of suspension in PBS or the like; perforated holes are formed on cell membrane surfaces with amphotericin B or the like; and ionic flows passing through ion channels present on cell surfaces are detected as currents.

In the present invention, the "fully automated high throughput patch clamp system" refers to an apparatus which sucks cells in suspension into a small hole in each well utilizing dropping by gravity and negative pressure, and to thereby make the recording of currents possible. Specific examples of fully automated high throughput patch clamp systems include IonWorks HT™ (Molecular Device) and PatchXpress™ 7000A (Axon Instruments).

In the present invention, hERG channel is one of the constituent proteins in the delayed rectifier potassium channel in cardiomyocytes and will be described later in detail.

In the present invention, hERG current refers to the flow of potassium ions passing through hERG channels present on cell membrane surfaces. The hERG channel is playing an important role in the heart to calm down electric excitement in cardiomyocytes. Drugs that inhibit the hERG current are compelled to withdraw from markets because such drugs involve a risk of inducing serious ventricular arrhythmia. Therefore, it has become essential to develop drugs that have no or extremely small effect on the hERG channel in development of new drugs.

In the present invention, the "hERG current as determined by patch clamping with a fully automated high throughput patch clamp system" means the ionic current observed when the membrane potential of hERG channel-expressing cells is changed. More specifically, the hERG current is the ionic current that is detected when the membrane potential of the cell is changed from −80 mV to +20 mV for 1 sec and then to −50 mV for 1 sec. The peak value of the tail current observed when the membrane potential is restored to −50 mV is taken as the amplitude of hERG current.

In the present invention, the "hERG channel-expressing cell" means a cell expressing hERG channels. Hereinbelow, a method of preparing a hERG channel-expressing cell or cell population will be described.

<hERG Channel>

In the present invention, the hERG channel to be expressed in cells contains a polypeptide containing an amino acid sequence identical or substantially identical with the amino acid sequence as shown in SEQ ID NO: 2 (GenBank Accession No. U04270) (hereinafter, sometimes referred to as the "polypeptide of the invention").

Hereinbelow, the polypeptide of the invention will be described in detail.

As the amino acid sequence substantially identical with the amino acid sequence as shown in SEQ ID NO: 2, an amino acid sequence which has about 90% or more, preferably about 95% or more, more preferably about 98% or more homology to the amino acid sequence as shown in SEQ ID NO: 2 and shows a polypeptide with hERG activity may be given.

In particular, in addition to the amino acid sequence above described, examples of the amino acid sequence substantially identical with the amino acid sequence as shown in SEQ ID NO: 2 include the amino acid sequence as shown in SEQ ID NO: 2 which has mutations such as deletion, substitution or addition in one or a plurality of (e.g., one or several) amino acids and shows a polypeptide with hERG activity.

Examples of the amino acid sequence as shown in SEQ ID NO: 2 which has mutations such as deletion, substitution or addition in one or a plurality of (e.g., one or several) amino acids include: (i) the amino acid sequence as shown in SEQ ID NO: 2 in which one to five (preferably one to three, more preferably one to two, still more preferably one) amino acids are deleted; (ii) the amino acid sequence as shown in SEQ ID NO: 2 to which one to five (preferably one to three, more preferably one to two, still more preferably one) amino acids are added; (iii) the amino acid sequence as shown in SEQ ID NO: 2 into which one to five (preferably one to three, more preferably one to two, still more preferably one) amino acids are inserted; (iv) the amino acid sequence as shown in SEQ ID NO: 2 in which one to five (preferably one to three, more preferably one to two, still more preferably one) amino acids are substituted with other amino acids; and (v) an amino acid sequence which is a combination of (i) to (iv) above.

Further, a mutant polypeptide composed of the amino acid sequence having deletion, insertion, substitution or addition of one or a plurality of amino acids and retains the same biological activity of the initial polypeptide is also included in the scope of the present invention (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; Dalbadie-McFarland et al. (1982) Proc. Natl. Acad. Sci. USA 79: 6409-13).

Substitution of amino acids means a mutation in which one or more of amino acid residues in an amino acid sequence are replaced with other amino acids. In the modification of the amino acid sequence encoded by the hERG gene of the invention by such substitution, it is preferable to carry out a conservative substitution when it is necessary to retain the function of the protein. Conservative substitution means to change a sequence so that the changed sequence encodes an amino acid similar to the replaced amino acid in nature. Amino acids may be classified into non-polar amino acids (Ala, Ile, Leu, Met, Phe, Pro, Trp, Val), uncharged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxylamino acids (Ser. Thr), amidic amino acids (Gln, Asn), sulfo-amino acids (Cys, Met), aromatic amino acids (His, Phe, Trp, Tyr), heterocyclic amino acids (His, Trp), imino acids (Pro, 4Hyp) and so on.

Therefore, it is preferable to carry out substitution between non-polar amino acids or between uncharged amino acids. Among all, substitutions between Ala, Val, Leu and Ile, between Ser and Thr, between Asp and Glu, between Asn and Gln, between Lys and Arg, and between Phe and Tyr are preferable for retaining the nature of the protein. The number and sites of amino acids to be mutated are not particularly limited.

Polynucleotides encoding the amino acid sequence as shown in SEQ ID NO: 2 having deletion, insertion, substitution or addition of one or a plurality of amino acids may be prepared according to methods such as site-specific mutagenesis described, for example, in "Molecular Cloning, A Laboratory Manual 2nd ed." (Cold Spring Harbor Press (1989)), "Current Protocols in Molecular Biology" (John Wiley & Sons (1987-1997); especially in Section 8.1-8.5), Hashimoto-Goto et al. (1995) Gene 152: 271-5, Kunkel (1985) Proc. Natl. Acad. Sci. USA 82: 488-92, Kramer and Fritz (1987) Method. Enzymol. 154: 350-67, and Kunkel (1988) Method. Enzymol. 85: 2763-6.

Introduction of mutations into polynucleotides may be performed by known methods such as the Kunkel method or the Gapped duplex method using, for example, QuikChange™ Site-Directed Mutagenesis Kit (Stratagene), GeneTailor™ Site-Directed Mutagenesis System (Invitrogen), or TaKaRa Site-Directed Mutagenesis System (Mutan-K, Mutan-Super Express Km).

Amino acid residues composing the polypeptide of the invention may be either naturally occurring amino acid residues or modified amino acid residues. Specific examples of modification of amino acid residues include acylation, acetylation, amidation, arginylation, GPI anchor formation, cross-linking, γ-carboxylation, cyclization, formation of covalent bridges, glycosylation, oxidation, covalent bonding to lipid or fat derivatives, formation of disulfide bonds, selenoylation, demethylation, degradation treatment of proteins, covalent bonding to nucleotides or nucleotide derivatives, hydroxylation, formation of pyroglutamate, covalent bonding to flavin, prenylation, covalent bonding to heme moieties, covalent bonding to phosphatidylinositol, formylation, myristoylation, methylation, ubiquitination, iodination, racemization, ADP-ribosylation, sulfation and phosphorylation.

Further, the polypeptide of the invention encompasses fusion proteins where other peptide sequences have been added. Peptide sequences to be added to the polypeptide of the invention may be selected from sequences that make the discrimination of the protein easy or sequences that give stability when the protein is expressed by recombinant DNA technology, e.g., influenza hemagglutinin (HA), glutathione S transferase (GST), substance P, multiple histidine tag (6×His, 10×His, etc.), protein C fragment, maltose binding protein (MBP), immunoglobulin constant region fragment, α-tubulin fragment, β-galactosidase, B-tag, c-myc fragment, E-tag (epitope on monoclonal phage), FLAG (Hopp et al. (1988) Bio/Tehcnol. 6: 1204-10), lck tag, p18 HIV fragment, HSV-tag (human herpes simplex virus glycoprotein), SV40T antigen fragment, T7-tag (T7 gene10 protein), VSV-GP fragment (Vesicular stomatitis virus glycoprotein), etc.

As the polypeptide of the invention, the above-described polypeptide may be enumerated. A preferable example of the polypeptide of the invention is a polypeptide which contains the amino acid sequence as shown in SEQ ID NO: 2 or an amino acid sequence substantially identical with the amino acid sequence as shown in SEQ ID NO: 2 and has a hERG activity substantially identical in nature with the hERG activity possessed by a polypeptide composed of the amino acid sequence as shown in SEQ ID NO: 2. The term "hERG activity" used herein means an activity of functioning as a potassium ion channel. The expression "activity substantially identical in nature" used herein means the relevant activity is identical in nature (e.g., physiochemically or pharmacologically).

<hERG Gene>

In the present invention, the "hERG gene" means a polynucleotide composed of a nucleotide sequence encoding a hERG channel. The hERG gene of the invention encompasses polynucleotides containing a nucleotide sequence identical or substantially identical with the nucleotide sequence as shown in SEQ ID NO: 1 (GenBank Accession No. U04270). A polynucleotide containing a nucleotide sequence substantially identical with the nucleotide sequence as shown in SEQ ID NO: 1 may be any polynucleotide as long as it has a nucleotide sequence encoding the above-described polypeptide of the invention. For example, in addition to polynucleotides encoding the amino acid sequence as shown in SEQ ID NO: 2, a polynucleotide encoding a mutant polypeptide composed of the amino acid sequence as shown in SEQ ID NO: 2 having deletion, insertion, substitution or addition of one or plurality of amino acids and has hERG activity may also be used in the present invention.

The term "polynucleotide" used herein refers to a polymer composed of a plurality of bases, such as deoxyribonucleic acid (DNA) or ribonucleic acid (RNA), or base pairs, and includes DNA, cDNA, genomic DNA, and chemically synthesized DNA and RNA. Polynucleotides optionally containing non-natural bases are also included in the term "polynucleotide". Specific examples of non-natural bases include 4-acetylcytidine, 5-(carboxyhydroxylmethyl)uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueosine, 5-methoxycarbonylmethyl-2-thiouridine, 5-methoxycarbonylmethyluridine, 5-methoxyuridine, 2-methylthio-N-6-isopentenyladenosine, N-((9-β-D-ribofuranosyl-2-methyltiopurine-6-yl)carbamoyl)threonine, N-((9-β-D-ribofuranosylpurine-6-yl)N-methyl-carbamoyl)threonine, uridine-5-oxyacetic acid-methyl ester, uridine-5-oxyacetic acid, wybutoxosine, pseudouridine, queosine, 2-thiocytidine, 5-methyl-2-thiouridine, 2-thiouridine, 4-thiouridine, 5-methyluridine, N-((9-β-D-ribofuranosylpurine-6-yl)carbamoyl)threonime, 2'-O-methyl-5-methyluridine, 2'-O-methyluridine, wybutosine and 3-(3-amino-3-carboxypropyl)uridine.

The hERG gene of the present invention encompasses genetic polymorphisms of the nucleotide sequence as shown in SEQ ID NO: 1. The genetic polymorphism may be easily known by using databases such as GenBank (http://www.ncbi.nlm.nih.gov). Genetic polymorphism includes single nucleotide polymorphism (SNP) and polymorphism caused by a varied number of nucleotide sequence repeats. Polymorphism caused by deletion or insertion of a plurality of nucleotides (e.g., two to several tens of nucleotides) is also included in genetic polymorphism. Besides, polymorphism where a sequence of two to several tens of nucleotides is repeated is also included in genetic polymorphism. Examples of these polymorphisms include VNTR (variable number of tandem repeat) (repeat unit composed of several to several tens of nucleotides) and micro-satellite polymorphism (repeat unit composed of about two to four nucleotides).

The hERG gene of the invention includes a nucleotide sequence encoding the amino acid sequence as shown in SEQ ID NO: 2. A nucleotide sequence encoding such an amino acid sequence encompasses, in addition to the nucleotide sequence as shown in SEQ ID NO: 1, nucleotide sequences which are different from SEQ ID NO: 1 because of the degeneracy of genetic codes. The nucleotide sequence as shown in SEQ ID NO: 1 from which non-coding regions are removed may also be used. When the polynucleotide of the invention is used for expressing a polypeptide by genetic engineering techniques, a nucleotide sequence with high expression efficiency may be selected and designed in view of the codon usage frequency in the cell to be used for expression (Grantham et al. (1981) Nucleic Acids Res. 9: 43-74).

Further, the hERG gene of the present invention encompasses a polynucleotide that hybridizes to the nucleotide sequence as shown in SEQ ID NO: 1 or a sequence complementary thereto under stringent conditions and encodes a polypeptide having hERG activity. Examples of such a polynucleotide include isoforms, alternative isoforms and allelic mutants; these are included in the hERG gene of the present invention. Such hERG genes may be obtained from human cDNA libraries or genomic libraries by a known hybridization method, such as colony hybridization, plaque hybridization or Southern blotting, using the polynucleotide composed of the nucleotide sequence as shown in SEQ ID NO: 1 or a fragment thereof as a probe. For methods for preparing cDNA libraries, see "Molecular Cloning, A Laboratory Manual 2nd Ed." (Cold Spring Harbor Press (1989)). Alternatively, commercial cDNA libraries or genomic libraries may be used.

More specifically, in the preparation of a cDNA library, first, total RNA is prepared from a cell, organ or tissue that is expressing the hERG gene of the invention by a known method such as the guanidine ultracentrifugation method (Chirwin et al. (1979) Biochemistry 18: 5294-9) or the AGPC method (Chomczynski and Sacchi (1987) Anal. Biochem. 162: 156-9). Then, mRNA is purified therefrom by using mRNA Purification Kit (Pharmacia) or the like. Alternatively, a kit such as Quick Prep mRNA Purification Kit (Pharmacia) may be used to prepare mRNA directly from cells, organs or tissues. Subsequently, cDNA is synthesized from the resultant mRNA with a reverse transcriptase. A cDNA synthesis kit such as AMV Reverse Transcriptase First-Strand cDNA Synthesis Kit (Seikagaku Corporation) may also be used. Alternatively, cDNA may be synthesized and amplified by 5'-RACE method utilizing PCR (Frohman et al. (1988) Proc. Natl. Acad. Sci. USA 85: 8998-9002; Belyavsky et al. (1989) Nucleic Acids Res. 17: 2919-32). It is also possible to employ a known technique such as oligo-capping method (Maruyama and Sugano (1994) Gene 138: 171-4; Suzuki (1997) Gene 200: 149-56) in order to prepare a cDNA library with a high full-length cDNA ratio. The cDNA obtained as described above may be incorporated into an appropriate vector.

In the hybridization conditions used in the present invention, stringent conditions may be, for example, (2×SSC, 0.1% SDS, 50° C.), (2×SSC, 0.1% SDS, 42° C.) or (1×SSC, 0.1% SDS, 37° C.); more stringent conditions may be, for example, (2×SSC, 0.1% SDS, 65° C.), (0.5×SSC, 0.1% SDS, 42° C.) or (0.2×SSC, 0.1% SDS, 65° C.). More specifically, hybridization using Rapid-hyb buffer (Amersham Life Science) may be performed as described below, for example. Pre-hybridization is performed at 68° C. for more than 30 min; then, a probe is added to the hybridization solution, which is retained at 68° C. for more than 1 hr to allow hybrid formation; then, washing is carried out in 2×SSC, 0.1% SDS at room temperature for 20 min three times, in 1×SSC, 0.1% SDS at 37° C. for 20 min three times, and finally in 1×SSC, 0.1% SDS at 50° C. for 20 min two times. Alternatively, for example, pre-hybridization is performed in Expresshyb Hybridization Solution (CLONTECH) at 55° C. for more than 30 min; a labeled probe is added to the solution, which is incubated at 37-55° C. for more than 1 hr; then, washing is carried out in 2×SSC, 0.1% SDS at room temperature for 20 min three times and in 1×SSC, 0.1% SDS at 37° C. for 20 min once. It is possible to make the hybridization conditions more stringent, for example, by raising the temperature of pre-hybridization, hybridization or second washing. For example, it is possible to set the temperature of pre-hybridization and hybridization at 60° C., or at 68° C. for more stringent conditions. Those skilled in the art can appropriately select the salt concentration and temperature of the buffer, as well as the concentration and length of the probe, reaction time, etc. to thereby set conditions for obtaining polynucleotides encoding the hERG gene of the invention.

For detailed procedures of hybridization, see "Molecular Cloning, A Laboratory Manual 2nd ed." (Cold Spring Harbor Press (1989); especially Section 9.47-9.58), "Current Protocols in Molecular Biology" (John Wiley & Sons (1987-1997); especially Section 6.3-6.4), "DNA Cloning 1: Core Techniques, A Practical Approach 2nd ed." (Oxford University (1995); especially, see Section 2.10 for conditions), and so forth. Examples of polynucleotides which hybridize to the nucleotide sequence as shown in SEQ ID NO: 1 or the sequence complementary thereto include polynucleotides containing a nucleotide sequence having 50% or more, preferably 70% or more, more preferably 80% or more, still more preferably 90% or more (e.g., 95% or more, or 99% or more) identity to the nucleotide sequence as shown in SEQ ID NO: 1. Such identity can be determined with BLAST algorithm (Altschul (1990) Proc. Natl. Acad. Sci. USA 87: 2264-8; Karlin and Altschul (1993) Proc. Natl. Acad. Sci. USA 90: 5873-7). Among programs based on this algorithm, there are programs for determining identity in sequences. BLASTX for amino acid sequence and BLASTN (Altschul et al. (1990) J. Mol. Biol. 215: 403-10) for nucleotide sequences have been developed and are available to the sequences of the present invention. For specific analyzing methods, see, for example, http://www.ncbi.nlm.nih.gov.

Genes whose structure and function are similar to those of hERG, such as isoforms or allelic mutants of hERG, (such genes are included in the hERG gene of the invention) may be obtained from human cDNA library or genomic library by using primers designed based on the nucleotide sequence as shown in SEQ ID NO: 1 and the gene amplification technique (PCR) (Current Protocols in Molecular Biology, John Wiley & Sons (1987) Section 6.1-6.4).

The polynucleotide of the invention encompasses polynucleotides encoding the amino acid sequence as shown in SEQ ID NO: 2 having deletion, insertion, substitution or addition of one or a plurality of amino acids, or sequences complementary to the sequences of these polynucleotides. These polynucleotides of the present invention may be prepared according to the site-specific mutagenesis method or the like described in "Molecular Cloning, A Laboratory Manual 2nd ed." (Cold Spring Harbor Press (1989)), "Current Protocols in Molecular Biology" (John Wiley & Sons (1987-1997); especially Section 8.1-8.5), Hashimoto-Goto et al. (1995) Gene 152: 271-5, Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6, etc. The above-described commercial kits may be used for mutagenesis.

Confirmation of the nucleotide sequence of the polynucleotide of the invention may be performed by sequencing using conventional methods. For example, the dideoxynucleotide chain termination method (Sanger et al. (1977) Proc. Natl. Acad. Sci. USA 74: 5463) may be used. Alternatively, the sequence may be analyzed with an appropriate DNA sequencer.

<Virus Vector Plasmids>

According to the present invention, virus vector plasmids containing the hERG gene of the invention (hereinafter, sometimes referred to as the "virus vector plasmid of the invention") are provided. The term "virus vector plasmid" refers to a plasmid which was engineered by using a virus-derived nucleotide sequence so that it is capable of integrating any nucleotide sequence into any cell. The virus vector plasmid of the invention is useful in retaining the hERG gene of the invention within host cells and allowing the expression of the hERG channel encoded by the hERG gene.

As viruses which will be the basis for virus vector plasmids, oncoretrovirus-derived viruses such as Moloney murine leukemia virus (MoMLV) and lentivirus-derived viruses such as human immunodeficiency virus (HIV) may be enumerated.

In the present invention, retrovirus refers to any virus belonging to the genus Oncovirus in the subfamily Oncovirinae in the family Retroviridae, and lentivirus refers to any virus belonging to the genus Lentivirus in the subfamily Lentivirinae in the family Retroviridae.

It has been already shown that use of retrovirus vectors or lentivirus vectors efficiently enables stable transfer of genes into chromosomes of cells and their expression (Kay, M. A. et al. Nature Med. vol. 7 33-40 (2001)). For the virus vector plasmid of the invention, various virus vector plasmids may be used. Specific examples include retrovirus vector plasmids such as pZIPneo (Cepko, C. L. et al. (1984) Cell. 37: 1053-1062), pBabePuro (Morgenstern, J. P. and Land, H. Nucleic Acids Res. vol. 18 3587-3596), pCLXSN (IMGENEX, catalog #10041P), ViraPort retroviral gene expression system (Stratagene, catalog #217563), pDON-AI (Takara, catalog #3650) and lentivirus vector plasmids such as pLenti6/V5-GW/lacZ (Invitrogen, Carlsbad, Calif., catalog #K4955-10). Further, virus vector plasmids prepared from viruses other than retrovirus and lentivirus may also be used. For example, vector plasmids prepared from adenovirus, adeno-associated virus, Sinbis virus, Sendai virus, togavirus, paramyxovirus, poxvirus, poliovirus, herpesvirus and vaccinia virus may be used.

Among retrovirus vectors, use of VSV-G pseudotyped retrovirus vectors is preferable. The term "pseudotyped" refers to a phenomenon in which the genome of one virus is budding surrounded by the envelope protein of other virus (Zavada, J., J. Gen. Virol. vol. 15 183-191 (1972)). Vesicular stomatitis virus (VSV) is a virus belonging to the family Rhabdoviridae and having a negative single-stranded RNA genome. It is believed that the receptor of its envelope protein (G protein) on the cell side is an anionic lipid such as phosphatidylserine (Schlegel, R. et al. Cell vol. 32 639-646 (1983); Mastromarino, P. et al. J. Gen. Virol. vol. 68 2359-2369 (1987)). It is reported that VSV-G pseudotyped retrovirus vector has an extremely broad host range compared to conventionally used amphotropic retrovirus vectors (Emi, N. et al., Proc. Natl. Acad. Sci. USA vol. 65 1202-1207 (1991); Arai, T. et al. Virol. vol. 260 109-115 (1999)) and that its gene transfer ability can be improved by ultracentrifugation (Burns, J. C. et al. Proc. Natl. Acad. Sci. USA vol. 90 8033-8037 (1993)). Therefore, by preparing a pseudotyped retrovirus having this VSV-G gene product as an envelope protein, it becomes possible to transfer the hERG gene into various cells more efficiently than achieved by retroviruses having their innate envelope protein.

The nature of these VSV-G pseudotyped vectors is the same in lentivirus vectors, and a large number of lentivirus vectors reported are pseudotyped vectors of this kind (Kay, M. A. et al. Nature Med. vol. 7 33-40 (2001)).

In a preferred embodiment of virus vector plasmids, a virus vector plasmid is linked to downstream region of regulatory sequences so that it comes to enable the expression of the hERG gene of the invention in a host cell into which the virus vector plasmid has been introduced. The "regulatory sequences" are promoter and terminator, and optionally contain trans-activator, transcription factor, poly-A signal that stabilizes transcript, splicing and polyadenylation signals, and the like. These regulatory sequences contain all the components necessary for the expression of the polynucleotide linked thereto.

The virus vector of the invention may contain selectable markers. Examples of selectable markers include drug resistance genes (neomycin resistance gene, hygromycin resistance gene, puromycin resistance gene, etc.) and fluorescent proteins (GFP, EGFP, etc.). Further, it is possible to integrate a signal peptide that is necessary for directing the intracellularly expressed polypeptide onto cell membranes into a virus vector plasmid so that the signal peptide is added to the polypeptide. Further, addition of linker and insertion of initiation codon (ATG) and termination codon (TAA, TAG or TGA) may be performed, if necessary.

When a mammalian cell or other animal cell is used as a host, adenovirus late promoter (Kaufman et al. (1989) Mol. Cell. Biol. 9: 946), CAG promoter (Niwa et al. (1991) Gene 108: 193-200), CMV immediate early promoter (Seed and Aruffo (1987) Proc. Natl. Acad. Sci. USA 84: 3365-9), EF1α promoter (Mizushima et al. (1990) Nucleic Acids Res. 18: 5322; Kim et al. (1990) Gene 91: 217-23), HSV TK promoter, SRα promoter (Takebe et al. (1988) Mol. Cell. Biol. 8: 466), SV40 promoter (Mulligan et al. (1979) Nature 277: 108), SV40 early promoter (Genetic Engineering Vol. 3, Williamson ed., Academic Press (1982) pp. 83-141), SV40 late promoter (Gheysen and Fiers (1982) J. Mol. Appl. Genet. 1: 385-94), RSV (Rous sarcoma virus)-LTR promoter (Cullen (1987) Methods Enzymol. 152: 684-704), MMLV-LTR promoter, CMV enhancer, SV40 enhancer, cPPT (central polypurine tract) sequence, globin intron, etc. may be used.

Insertion of the hERG gene into virus vector plasmids may be performed by ligase reaction. At this time, restriction enzyme sites may also be used (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63).

<Preparation of Virus Vectors>

In the present invention, the term "virus vector" means a virus containing a virus vector plasmid. For the preparation of a virus vector, a virus vector plasmid is introduced into a packaging cell. As a packaging cell, 293-EBNA cells (Invitrogen, catalog #R620-07) or the like may be used. A virus vector plasmid may be introduced into a packaging cell by various methods such as the adenovirus method, electroporation (Cytotechnology 3: 133 (1990)), the cationic liposome method (cationic liposome DOTAP (Boehringer Mannheim), etc.), the method using a positively charged polymer, the electrostatic type liposome method, the internal type liposome method, particle gun bombardment, the liposome method, lipofection (Proc. Natl. Acad. Sci. USA 84: 7413 (1987) (e.g., lipofectamine 2000 (Invitrogen), Fugene 6 (Roche Diagnostics), etc.)), the calcium phosphate method (JP 2-227075 A), receptor-mediated gene transfer, the retrovirus method, the DEAE dextran method, the virus-liposome method (Experimental Medicine additional volume "Basic Technology for Gene Therapy", Yodo-sha (1997); Experimental Medicine additional volume "Analytical Experiments on Gene Transfer and Expression", Yodo-sha (1997); J. Clin. Invest. 93: 1458-64 (1994); Am. J. Physiol. 271: R1212-20 (1996); Molecular Medicine 30: 1440-8 (1993); Experimental Medicine 12: 1822-6 (1994); Protein, Nucleic Acid and Enzyme, 42: 1806-13 (1997); Circulation 92 (Suppl. II): 479-82 (1995)) and direct transfer of naked-DNA.

Briefly, a virus vector may be obtained by culturing a packaging cell in an appropriate medium, transfecting a virus vector plasmid into the cell by the above-mentioned method, then culturing the cell for a specific period of time, and recovering the resultant culture. After the transfection, if necessary, the medium may be exchanged 2 to 24 hours, preferably 6 to 12 hours thereafter. After the medium exchange, the cell is cultured for another 12 to 72 hours. Then, a virus vector can be obtained by recovering the culture. If necessary, the recovered culture may be centrifuged or filtered with, for example, a 0.45 μm filter (Millipore, MILLEX-WV, catalog #SLHV025LS).

<Concentration of Virus Vectors>

Although the virus vector of the invention may be used as it is, it is preferable to concentrate the virus vector. A concentrated virus vector may be obtained by ultracentrifuging the virus vector obtained by the above-described procedures. Ultracentrifugation is performed at least at 35,000 g (g represents gravitational acceleration) or more, preferably 55,000 g or more, at least for 100 min or more, preferably 120 min or more. Ultracentrifugation can be achieved, for example, with an ultracentrifuge XL-90 (Beckman) and an ultracentrifuge rotor SW28 (Beckman) at 19,500 rpm for 100 min.

<hERG Gene Transfer>

In the present invention, the hERG gene transfer into cells may be performed by using the virus vector of the invention as it is. However, use of a concentrated virus vector is preferable.

As a host cell in the hERG channel-expressing cell or hERG channel-expressing cell population of the invention, a mammal-derived eukaryotic cell may be used. Preferably, CHO cells (especially, DHFR gene deficient dhfr⁻ CHO (Proc. Natl. Acad. Sci. USA 77: 4216-20, 1980) and CHO K-1 (Proc. Natl. Acad. Sci. USA 60: 1275, 1968) are preferable), COS cells, Hela cells, C127 cells, 3T3 cells, BHK cells, HEK293 cells, Bowes melanoma cells and the like may be used. It is also possible to use a heart-derived cell line or an isolated cardiomyocyte or sinoatrial node cell as a host cell in the hERG channel-expressing cell or hERG channel-expressing cell population of the invention. The hERG channel-expressing cell or cell population of the invention also includes those cells which are capable of regulating transcription and thereby regulating expression under specific conditions (e.g., under drug stimulation, electric stimulation, thermal stimulation, photo stimulation, or the like).

Gene transfer can be achieved by culturing a host cell, adding a virus vector to the culture, and culturing further. Preferably, a concentrated virus vector is used. If necessary, polybrene (Sigma H9268, also known as hexadimethrine bromide) may be added to the virus vector to be added to the culture. Twenty-four hours after the addition of the virus, it is preferable to exchange the medium. It is possible to make the expression level per cell highest by culturing the cell for about 72 hours after the medium exchange.

<hERG Channel-Expressing Cell and hERG Channel-Expressing Cell Population>

By the procedures described so far, the hERG channel-expressing cell or hERG channel-expressing cell population of the invention is provided. Culture is performed by a known method suitable for the selected cell. For example, medium such as DMEM, MEM, RPMI1640, IMDM or F12 may be used. If necessary, serum such as fetal calf serum (FCS), amino acid, glucose, penicillin or streptomycin, and the like may be added thereto. The cell may be cultured at about pH 6-8 at 30-40° C. for about 15-200 hours. During the course of culture, medium may be exchanged, and aeration and agitation may be carried out if necessary.

In the cell population of hERG gene-transferred cells obtained by the method of the invention (hereinafter, sometimes referred to as the "hERG channel-expressing cell population of the invention"), a large number of channel-expressing cells (hereinafter, referred to as the "hERG channel-expressing cell of the invention") are present. Inter alia, the hERG channel-expressing cell population of the invention contains a plenty of hERG channel expressing cells of which the hERG current as determined by patch clamping with a fully automated high throughput patch clamp system is 0.6 nA or more. The ratio of such cells in the total number of hERG gene-transferred cells is at least 40% or more, preferably 50% or more, more preferably 60% or more, especially preferably 70% or more, and most preferably 80% or more. With respect to the hERG gene-transferred cells, as long as the contents of gene transfer operations are the same, the total number of cells into which the gene was transferred in the same experiment system may be taken as the parameter, or cells into which the gene was transferred in different experiment systems (e.g., experiments conducted on different days) may be summed up and the total may be taken as the parameter. The average amplitude of hERG currents in the hERG channel-expressing cell population is 0.3 nA or more, preferably 0.6 nA or more, more preferably 0.8 nA or more, still more preferably 1.0 nA or more.

The hERG current of the hERG channel-expressing cell or hERG channel-expressing cell population as determined by patch clamping with a fully automated high throughput patch clamp system may be determined by the patch clamp technique described later. The ratio of hERG channel-expressing cells of which the hERG current as determined by patch clamping with a fully automated high throughput patch clamp system is 0.6 nA or more can be obtained by selecting a plurality of cells at random, measuring the hERG current of each of these cells, and then calculating the ratio of those cells of which the hERG current is 0.6 nA or more.

The hERG channel-expressing cell or hERG channel-expressing cell population of the invention also encompasses those cells or cell strains obtained by the cloning described later. Further, the hERG channel-expressing cell or hERG channel-expressing cell population of the invention also encompasses those cells or cell populations that are obtained by transferring the hERG gene again into the cell strain obtained by the cloning.

<Cloning of hERG Channel-Expressing Cell>

Although the hERG channel-expressing cell or hERG channel-expressing cell population of the invention may be used as it is, the cell or the cell population may be subjected to cloning in order to avoid bias in nature during culture and to enable stable evaluation of drugs. Cell cloning may be performed according to conventional methods (such as the limiting dilution culture method or cell sorting by flow cytometry). It is possible to select from the cloned cell strains hERG channel-expressing cell strains which are more suitable for measurement of expression levels and functional analysis of hERG channel by the patch clamp technique.

hERG channel expression levels in hERG channel-expressing cells may be determined by immunohistological analysis methods using anti-hERG channel antibody. The antibodies may be prepared according to conventional methods. Alternatively, a commercial antibody (such as prepared by Alomene Labs) may be used. Examples of immunohistological analysis methods include enzyme immunoassay (EIA), radioimmunoassay (RIA), ELISA, Western blotting, flow cytometry, and immunohistochemical staining.

By this cloning, cells of which the hERG current as determined by patch clamping with a fully automated high throughput patch clamp system is at least 0.4 nA or more, preferably 0.6 nA or more, more preferably 0.8 nA or more, still more preferably 1.0 nA or more, especially preferably 1.2 nA or more, are provided more easily.

<Method of Measurement of hERG Currents>

The present invention provides a method of measuring hERG currents by using the hERG channel-expressing cell or hERG channel-expressing cell population of the invention. More specifically, the present invention provides a method of measuring hERG currents using the hERG channel-expressing cell or hERG channel-expressing cell population of the invention by the patch clamp technique, preferably with a fully automated high throughput patch clamp system, A hERG channel-expressing cell or hERG channel-expressing cell population may be obtained by the above-described method of preparing the hERG channel-expressing cell of the invention. For the hERG channel expression level of the hERG channel expressing cell used in the method of measurement of hERG currents of the invention, the channel current as determined by patch clamping with a fully automated high throughput patch clamp system is preferably at least 0.4 nA or more, preferably 0.6 nA or more, more preferably 0.8 nA or more, still more preferably 1.0 nA or more, especially preferably 1.2 nA or more. Such a hERG channel-expressing cell or hERG channel-expressing cell population is also included in the scope of the present invention. It should be noted here that the higher the expression level is, the higher the channel current as determined by patch clamp technique becomes.

For practicing the method of measuring hERG currents of the invention, the hERG channel-expressing cell or cell population of the invention is cultured for a specific period of time by the appropriate method as described above and suspended in a buffer suitable for measurement. As the buffer, any buffer which does not affect hERG currents may be used, e.g., phosphate buffer or Tris-HCl buffer at pH 6-8. Preferably, phosphate buffered saline (pH 7.4) is used.

Subsequently, hERG currents may be recorded by the patch clamp technique, preferably with a fully automated high throughput patch clamp system. hERG currents may be induced by giving various holding potentials and depolarizing pulses to cells. These conditions may be easily set by those skilled in the art (Zhou, Z. et al., Biophysical Journal, 74, 230-241 (1998)). For example, hERG currents may be induced by changing the holding potential from −80 mV to +20 mV for 1 sec and then applying a depolarizing pulse to −50 mV for 1 sec. As the amplitude of hERG current, the peak value of the tail current observed when the potential is restored to −50 mV may be used.

<Method of Measuring hERG Current Inhibitory Activities Using the hERG Channel-Expressing Cell of the Invention>

It is known that compounds with hERG current inhibitory activity have arrhythmogenesis effect accompanied by QT interval prolongation effect. Such compounds may induce serious adverse effects such as ventricular tachycardia or sudden death. Therefore, in the development of highly safe pharmaceuticals, it is essential to confirm that the test substance (target of development) does not affect hERG currents. The method of measuring hERG current inhibitory activities using the hERG channel-expressing cell of the invention facilitates the selection of test compounds that do not affect hERG currents. Therefore, the method of measuring inhibitory activities of the invention is useful in developing pharmaceuticals such as therapeutics and prophylactics for various diseases.

The present invention provides a method of measuring hERG current inhibitory activities by using a hERG channel-expressing cell or a hERG channel-expressing cell population. Specifically, the present invention provides a method of measuring hERG current inhibitory activities by contacting a test compound with the hERG channel-expressing cell or cell population of the invention. In the measurement of hERG current inhibitory activities of the present invention, it is possible to measure hERG currents of the hERG channel-expressing cell or cell population of the invention before and after contacting a test compound with the cell or cell population, and compare the results. For example, hERG current inhibitory activities may be determined by using as an indicator the ratio of the amplitude of hERG current after contacting a test compound to the amplitude of hERG current before contacting the test compound.

The present invention further provides a method of screening for compounds, or salts thereof, that alter or do not alter hERG currents, by using a hERG channel-expressing cell or cell population. Specifically, the present invention provides a method of screening for compounds, or salts thereof, that alter or do not alter hERG currents, by comparing the case of contacting a test compound with the hERG channel-expressing cell or cell population of the invention and the case of not contacting the test compound with the cell or cell population. In the screening method of the present invention, it is possible to measure hERG currents of the hERG channel-expressing cell or cell population of the invention in the case of contacting and in the case of non-contacting, and to compare the results. For example, when the hERG current in the case of contacting the test compound is smaller than the hERG current in the case of non-contacting the test compound, the test compound can be regarded as a hERG channel current inhibitory compound.

As the hERG channel-expressing cell or cell population, the hERG channel-expressing cell of the invention or the hERG channel-expressing cell population of the invention may be used. Alternatively, such a cell or cell population may be obtained by the method of the invention for preparing a hERG channel-expressing cell or cell population described above. In the method of measuring hERG current inhibitory activities of the invention, for the hERG channel expression level of the hERG channel expressing cell or cell population of the invention, the channel current as determined by patch clamping with a fully automated high throughput patch clamp system is at least 0.4 nA or more, preferably 0.6 nA or more, more preferably 0.8 nA or more, still more preferably 1.0 nA or more, especially preferably 1.2 nA or more. It should be noted here that the higher the expression level is, the higher the channel current as determined by the patch clamp technique becomes; thus, construction of a more sensitive measuring system becomes possible.

In order to practice the method of the invention described above, the hERG channel-expressing cell or cell population of the invention is cultured for a specific period of time by the appropriate method as described above and suspended in a buffer suitable for measurement. As the buffer, any buffer which does not affect hERG currents may be used, e.g., phosphate buffer or Tris-HCl buffer at pH 6-8. Preferably, phosphate buffered saline (pH 7.4) is used.

First, hERG currents may be recorded by the patch clamp technique, preferably with a fully automated high throughput patch clamp system. hERG currents may be induced by giving various holding potentials and depolarizing pulses to cells. These conditions may be easily set by those skilled in the art. For example, hERG currents may be induced by changing the holding potential from −80 mV to +20 mV for 1 sec and then applying a depolarizing pulse to −50 mV for 1 sec. As the amplitude of hERG current, the peak value of the tail current observed when the potential is restored may be used.

Subsequently, a test compound is allowed to co-exist with the hERG channel-expressing cell. At this time, the cell without the test compound and the cell with compounds which are known to inhibit hERG currents may also be prepared as controls. Specific examples of compounds that inhibit hERG currents include astemizole (Talialatel et al. (1998) Mol. Pharmacol. 54: 113-21), E-4031 (Zhou et al. Biophys. J. (1998) 74: 230-41), risperidone (Kongsamut et al. Eur. J. Pharmacol. (2002) 450: 37-41), verapanil (Zhang et al. (1999) Circ. Res. 84: 989-98) and quinidine (Jiesheng et al. J. Pharmacol. Exp. Ther. (2001) 299: 290-6). The reaction is performed, for example, at 15-37° C., preferably at 20-30° C., for 10 sec to 60 min, preferably for 3 min to 10 min.

Then, hERG currents may be recorded by the patch clamp technique, preferably with a fully automated high throughput patch clamp system. hERG currents may be induced under the same conditions as used before the co-existence with the test compound. As the amplitude of hERG current the peak value of the tail current observed when the potential is restored may be used.

For example, the amplitude of the hERG current before the contact with the test compound is taken as 100% and 0 nA is taken as 0%. Then, inhibition ratio is calculated from the amplitude of the hERG current after the contact with the test compound, followed by determination of the hERG current inhibitory activity of the test compound. Further, it is also possible to calculate the inhibitory activity value inherent in the test compound by varying the dose of the test compound. When the concentration of the test compound inducing 50% inhibition of hERG currents is at least 0.3 µM or more, preferably 1.0 µM or more, more preferably 3.0 µM or more, especially preferably 10 µM or more, most preferably 30 µM or more, the test compound can be judged as not affecting hERG currents or not having inhibitory activity.

Examples of test compounds include peptides, proteins, non-peptidic compounds, synthetic compounds, fermentation products, cell extracts, plant extracts and animal tissue extract. These compounds may be either novel compounds or known compounds.

<Method of Measuring Changes in Membrane Potential on hERG Channel-Expressing Cell of the Invention with FLIPR Membrane Potential Assay Kit>

The present invention provides a method of measuring changes in membrane potential on the hERG channel-expressing cell using FLIPR Membrane Potential Assay Kit (Molecular Devices).

Specifically, changes in membrane potential may be measured by performing the following operations in a manner as described below. The hERG channel-expressing cell of the invention is cultured for a specific period of time by the appropriate method as described above and suspended in a buffer suitable for measurement. As the buffer, any buffer which does not affect hERG currents may be used, e.g., phosphate buffer or Tris-HCl buffer at pH 6-8. Preferably, phosphate buffered saline (pH 7.4) is used. It is preferred that the cell suspension be prepared to give a concentration of $0.2 \times 10^5$ cells/ml to $1.0 \times 10^6$ cells/ml. Subsequently, the cell suspension is plated on plates (such as Biocoat Poly-D-Lysine 384-Well Black/Clear Plate; BECKTON DICKINSON) and cultured further Cells may be plated at 500 cells/well to 25000 cells/well. Preferably, cells are cultured for about two days after the plating. Subsequently, Component A contained in FLIPR Membrane Potential Assay Kit (Molecular Devices) is dissolved in a measurement buffer (130 mM NaCl, 5 mM KCl, 1 mM $MgCl_2$, 1 mM $CaCl_2$, 24 mM Glucose, 10 mM HEPES (final pH: approx. 7.25)), and a 25 µl aliquot of this solution is added to each well. About one hour after the addition of Component A, changes in membrane potential may be measured with FLIPR (Molecular Devices) or FDSS6000 (Hamamatsu Photonics). As the measuring program, the appropriate condition may be set by those skilled in the art. For example, measurement may be performed 10 times before the addition of a test compound and 50 times after the addition, both at 6 second intervals. Measurement may be performed at room temperature. hERG inhibitory activity may be calculated from the change in fluorescence intensity caused by the addition of the test compound. As positive controls, E4031, Dofetilide and the like may be used.

In the specification and drawings of the present application, the abbreviations used for nucleotides, amino acids and so forth are those recommended by the IUPAC-IUB Commission on Biochemical Nomenclature or those conventionally used in the art. Examples of such abbreviations are given below. Amino acids that may have optical isomers are intended to represent their L-isomer unless otherwise specified.

DNA: Deoxyribonucleic acid
cDNA: Complementary deoxyribonucleic acid
A: Adenine
T: Thymine G: Guanine
C: Cytosine
RNA: Ribonucleic acid
mRNA: Messenger ribonucleic acid
Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R: Arginine
His or H: Histidine
Phe or F: Phenylalanine
Tyr or Y: Tyrosine
Trp or W: Tryptophan
Pro or P: Proline
Asn or N: Asparagine
Gln or Q: Glutamine The sequence ID numbers in the sequence listing of the specification of the present patent application represent the following sequences.

[SEQ ID NO: 1] This shows the nucleotide sequence represented by GenBank Accession No. U04270.
[SEQ ID NO: 2] This shows the amino acid sequence represented by GenBank Accession No. U04270.
[SEQ ID NO: 3] This shows the nucleotide sequence of a primer for cloning hERG gene.
[SEQ ID NO: 4] This shows the nucleotide sequence of a primer for cloning hERG gene.
[SEQ ID NO: 5] This shows the nucleotide sequence of a primer for cloning hERG gene.
[SEQ ID NO: 6] This shows the nucleotide sequence of a primer for cloning hERG gene.
[SEQ ID NO: 7] This shows the nucleotide sequence of a primer for cloning hERG gene.
[SEQ ID NO: 8] This shows the nucleotide sequence of a primer for cloning hERG gene.
[SEQ ID NO: 9] This shows a nucleotide sequence to insert a multicloning site.
[SEQ ID NO: 10] This shows a nucleotide sequence to insert a multicloning site.
[SEQ ID NO: 11] This shows a nucleotide sequence to insert a central polypurine tract.
[SEQ ID NO: 12] This shows a nucleotide sequence to insert a central polypurine tract.
[SEQ ID NO: 13] This shows the nucleotide sequence of pBabe Puro.

EXAMPLES

Hereinbelow, the present invention will be described in more detail with reference to the following Examples. However, the present invention is not restricted to these Examples.

Example 1

Preparation of hERG Gene

A hERG gene was isolated as described below by using the nucleotide sequence as shown in SEQ ID NO: 1 as a basis. In this sequence, 4070 bps are shown in which the region encoding a hERG channel (excluding the stop codon) is said nucleotides 184 to 3660 (3477 bps, 1159 amino acid residues) (GenBank Accession No. U04270). In order to isolate the gene by PCR (polymerase chain reaction), oligo DNA primers as shown in SEQ ID NO: 3 to 8 were prepared by Japan Bio Service (Asaka City, Saitama) upon request of the inventors.

cDNA was prepared by using human brain polyA+ RNA (Clontech, Palo Alto, Calif., catalog #6516-1) as a template with Superscript First-Strand Synthesis System (Invitrogen/Gibco, Md.). Subsequently, by using the resultant cDNA as a template and oligo DNAs consisting of SEQ ID NO: 3 and 4, SEQ ID NO: 5 and 6 and SEQ ID NO: 7 and 8 as primers, PCR reactions were performed with Expand High Fidelity PCR System (Roche Diagnostics, Mannheim, Germany) by repeating 30 cycles of 95° C. for 30 sec, 61° C. for 30 sec and 68° C. for 1 min. The nucleotide sequences of the primers are as described below.

```
Primer:
AATTGGTACCATGGGCTCAGGATGCCGGTGC    (SEQ ID NO: 3)

Primer:
GCTTGTACTCAGGCAGCACGT              (SEQ ID NO: 4)

Primer:
CCACCAGTGACCGTGAGATCA              (SEQ ID NO: 5)

Primer:
TTGCAGTGCTGCAGCAGTGAG              (SEQ ID NO: 6)

Primer:
ATGCTAGCATCTTCGGCAACG              (SEQ ID NO: 7)

Primer:
AATTAAGCTTTTCGAGTTCCTCTCCCTTC      (SEQ ID NO: 8)
```

As a result, DNA fragments of approx. 1.2 kb, 1.2 kb and 1.6 kb, respectively, were obtained.

These DNA fragments were inserted into pT7Blue (Novagen, Darmstadt, Germany, catalog #69967-3) and sequenced by using ABI prism DNA sequencing kit (Perkin-Elmer Applied Biosystems, Foster City, Calif.) for confirmation. As a result, a 1179 bps sequence obtained with the primer pair consisting of SEQ ID NO: 3 and 4 was identical with the nucleotides 173 to 1351 in SEQ ID NO: 1. On the other hand, a 1168 bps sequence obtained with the primer pair consisting of SEQ ID NO: 5 and 6 had two mutations (A1875G and T2149C). It is clear that these mutations do not influence the amino acids translated from the nucleotide sequences of the relevant sites (Leu and Thr). A 1642 bps sequence obtained with the primer pair consisting of SEQ ID NO: 7 and 8 also had two mutations (C2420T and A3367G). Since a plurality of clones obtained this time had the same mutations, it was judged that this sequence was correct as a hERG gene in the sample used this time (human brain polyA+ RNA (Clontech, Palo Alto, Calif., catalog #6516-1)).

pBluescript (Stratagene, La Jolla, Calif.) was digested with restriction enzymes KpnI and XhoI. On the other hand, the DNA fragment obtained with the primer pair consisting of SEQ ID NO: 3 and 4 was digested with restriction enzymes KpnI and BstEII, and the DNA fragment obtained with the primer pair consisting of SEQ ID NO: 5 and 6 was digested with restriction enzymes BstEII and XhoI. Subsequently, the resultant DNA fragments were inserted into the KpnI/XhoI-digested pBluescript by ligase reaction (TaKaRa, Cat. 6022) to thereby prepare pBS-1& 14&15& 18.

pBluescript was digested with restriction enzymes HindIII and XhoI. On the other hand, the DNA fragment obtained with the primer pair consisting of SEQ ID NO: 7 and 8 was digested with restriction enzymes HindIII and SacI. The resultant DNA fragment was inserted into the HindIII/XhoI-digested pBluescript by ligase reaction to thereby prepare pBS-6&4.

Further, pREP7 (Invitrogen, Carlsbad, Calif.) was digested with KpnI and HindIII. On the other hand, pBS-1&14&15&18 was digested with KpnI and XhoI, and pBS-6&4 was digested with XhoI and HindIII. The resultant DNA fragments were inserted into KpnI/HindIII-digested pREP7 by ligase reaction to thereby obtain pREP7hERG containing a hERG gene.

Example 2

Figure 2:
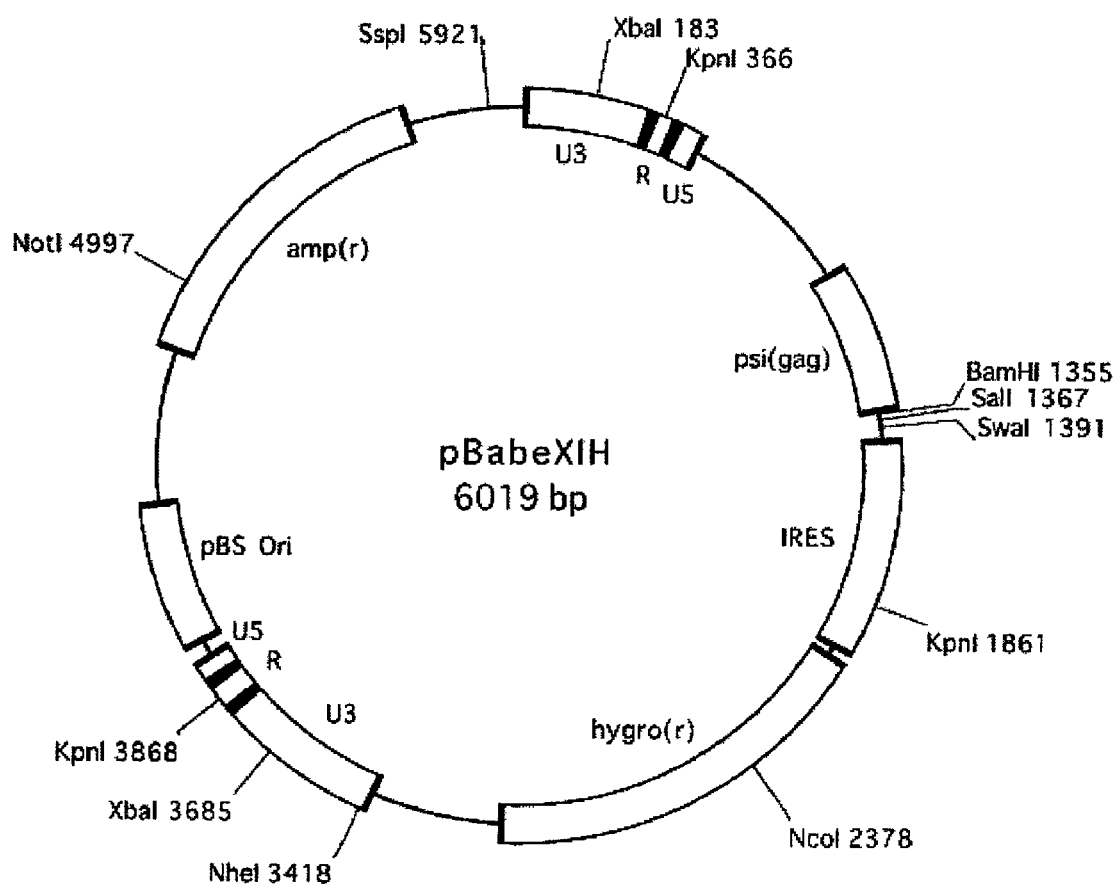
FIG. 2 shows the structure of a retrovirus vector plasmid (pBabeXIH).
Figure 3:
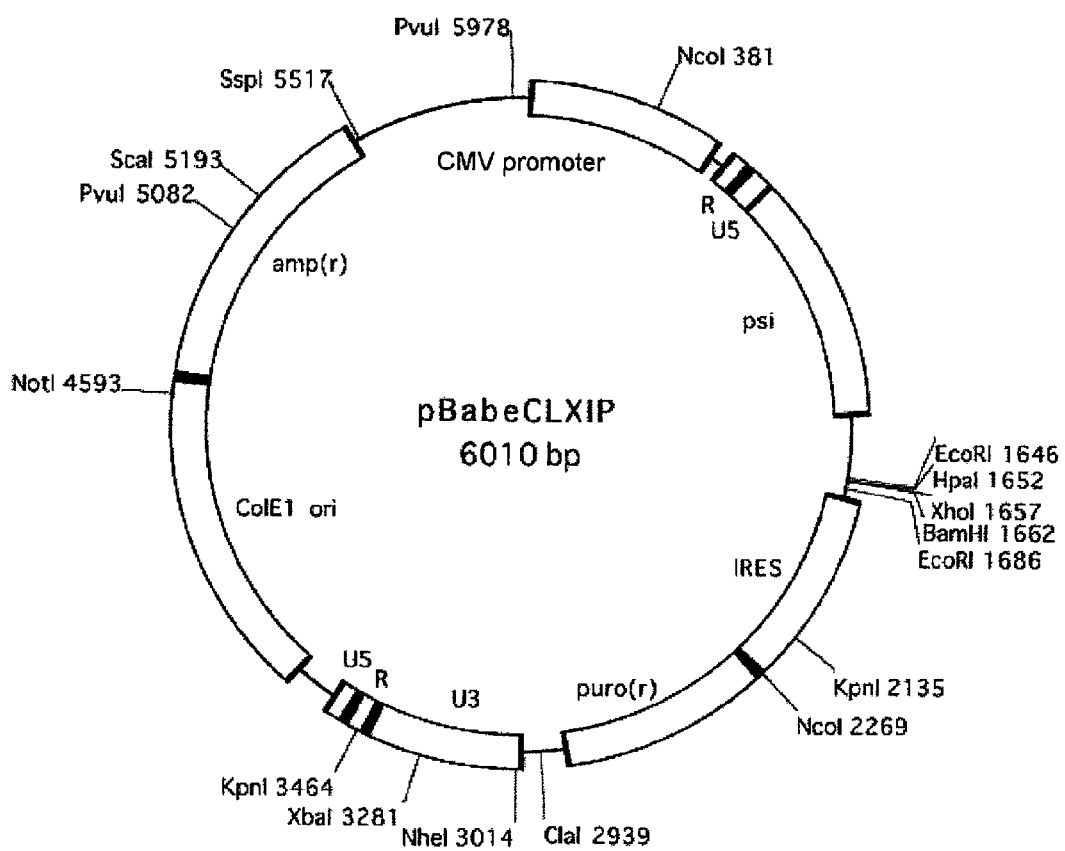
FIG. 3 shows the structure of a retrovirus vector plasmid (pBabeCLXMP).
Figure 4:
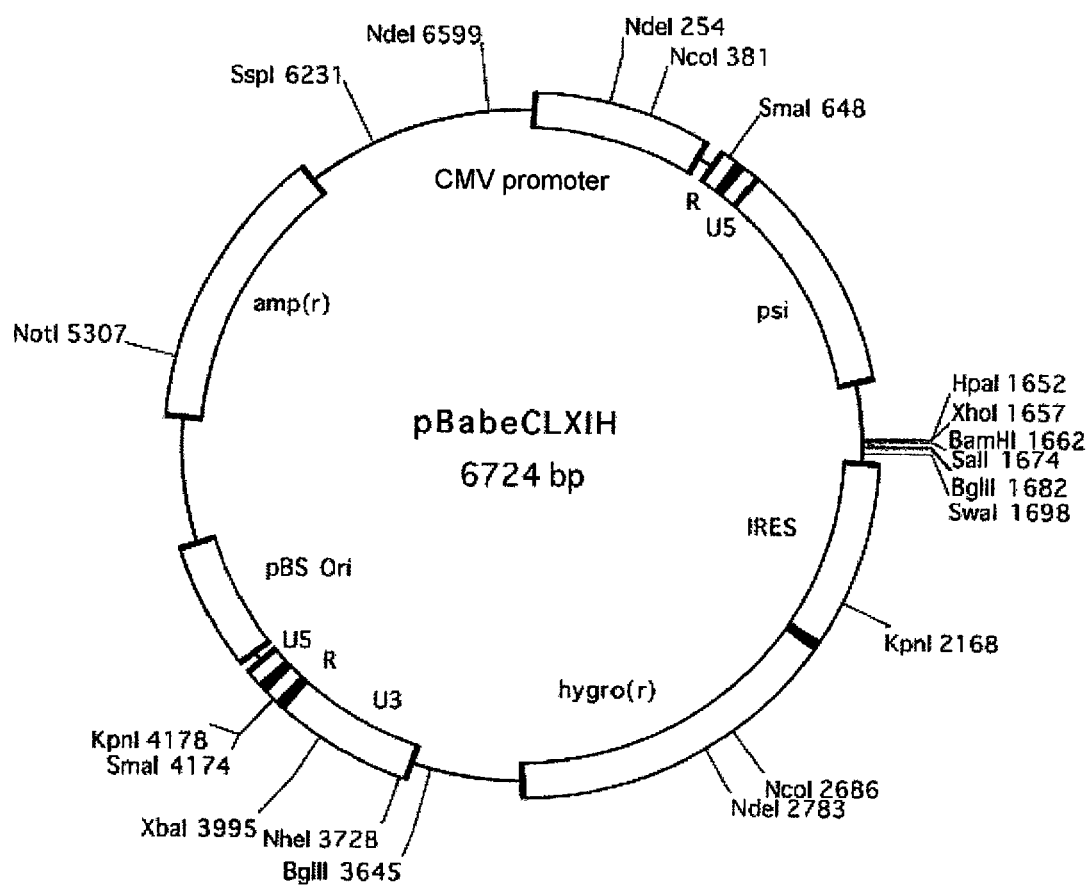
FIG. 4 shows the structure of a retrovirus vector plasmid (pBabeCLXIH).
Figure 5:
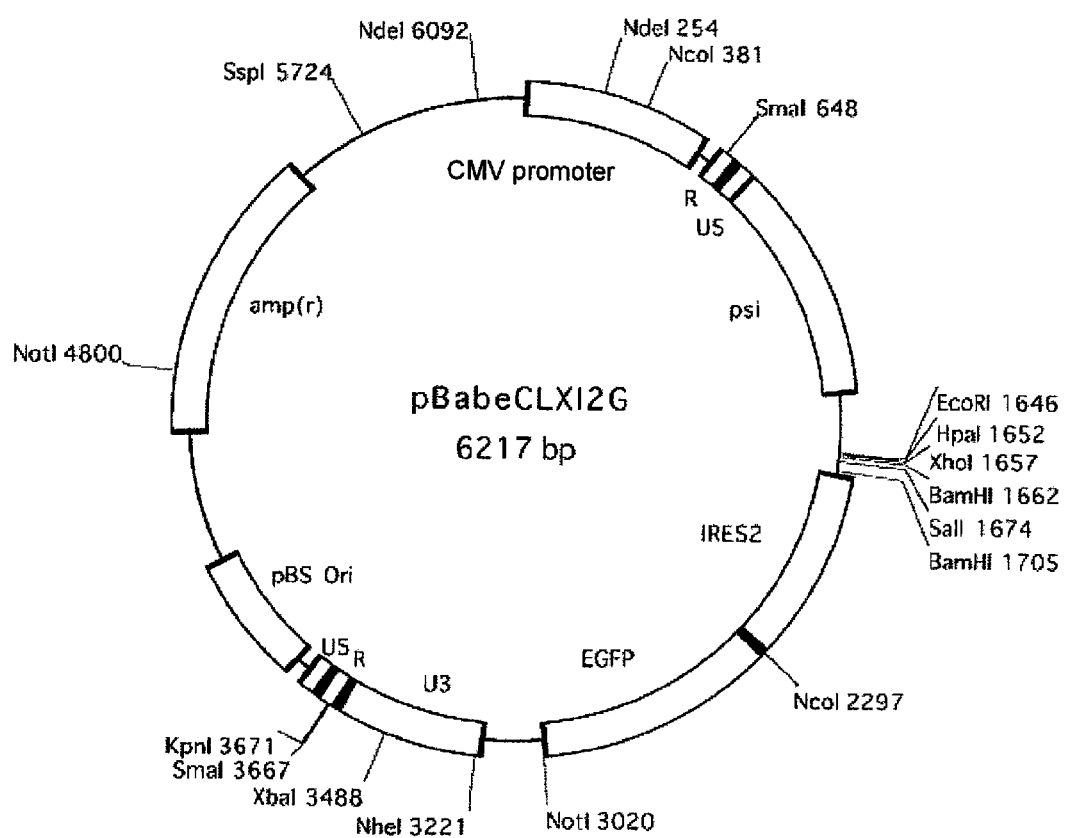
FIG. 5 shows the structure of a retrovirus vector plasmid (pBabeCLXI2G).
Figure 6:
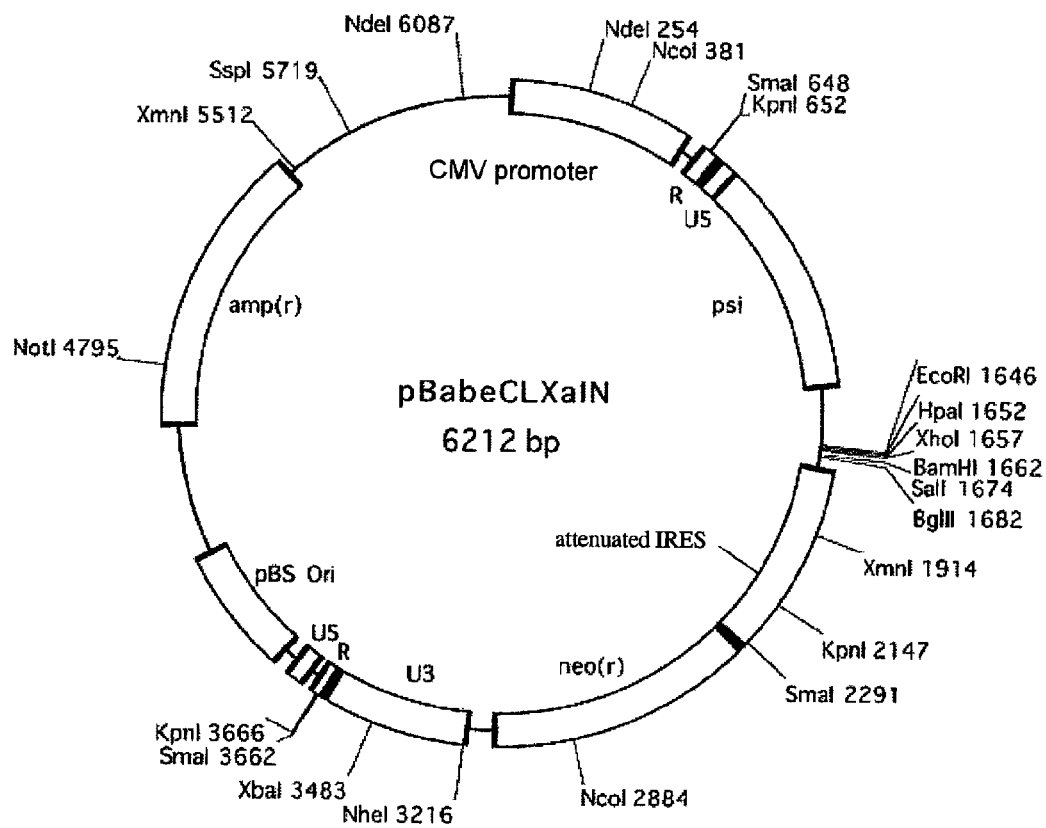
FIG. 6 shows the structure of a retrovirus vector plasmid (pBabeCLXaIN).

Preparation of Retrovirus Vector Plasmids pBabe Puro (Morgenstern, J. P. and Land, H., Nucleic Acids Res. vol. 18 3587-3596) (SEQ ID NO: 13) was digested with restriction enzymes SalI and ClaI to remove SV40 promoter-puro(r) and then blunt-ended with Klenow fragment (Takara, Otsu, Japan). Into this site, IRES-puro(r) that had been cut out from pRESpuro (Clontech, Palo Alto, Calif., catalog #6031-1) with restriction enzymes NsiI and XbaI and then blunt-ended with T4 polymerase was inserted to thereby obtain pBabeXIP (FIG. 1).

pBabe Puro (Morgenstern, J. P. and Land, H., Nucleic Acids Res. vol. 18 3587-3596) (SEQ ID NO: 13) was digested with SalI and ClaI to remove SV40 promoter-puro(r) and then blunt-ended with Klenow fragment. Into this site, IRES-hyg(r) that had been cut out from pIREShyg (Clontech, Palo Alto, Calif., catalog #6061-1) with restriction enzymes NsiI and XbaI and then blunt-ended with T4 polymerase was inserted to thereby obtain pBabeXIH (FIG. 2).

pBabeXIP was digested with restriction enzymes SspI and BamHI to remove 5'-LTR-packaging signal. Into this site, 5'LTR-CMV promoter-packaging signal that had been cut out from pCLXSN (IMGENEX San Diego, Calif., catalog #10041P) with restriction enzymes SspI and BamHI was inserted to thereby obtain pBabeCLXIP (FIG. 3).

pBabeXIH was digested with SspI and BamHI to remove 5'-LTR-packaging signal. Into this site, 5'LTR-CMV promoter-packaging signal that had been cut out from pCLXSN (IMGENEX San Diego, Calif., catalog #10041P) with SspI and BamHI was inserted to thereby obtain pBabeCLXIH (FIG. 4).

pBabeCLXIH was digested with restriction enzyme BglII to remove IRES-hyg(r) and then blunt-ended with Klenow fragment. Into this site, IRES-EGFP that had been cut out from pIRES2-EGFP (Clontech, Palo Alto, Calif., catalog #6029-1) with restriction enzyme HincII was inserted to thereby obtain pBabeCLXI2G (FIG. 5).

pBabeCLXIH was digested with BglII to remove IRES-hyg(r) and then blunt-ended with Klenow fragment. Into this site, IRES-neo(r) that had been cut out from pIRES2-neo2 (Clontech, Palo Alto, Calif., catalog #6938-1) with NsiI and XbaI and then blunt-ended with T4 polymerase was inserted to thereby obtain pBabeCLXaIN (FIG. 6).

Example 3

Figure 7:
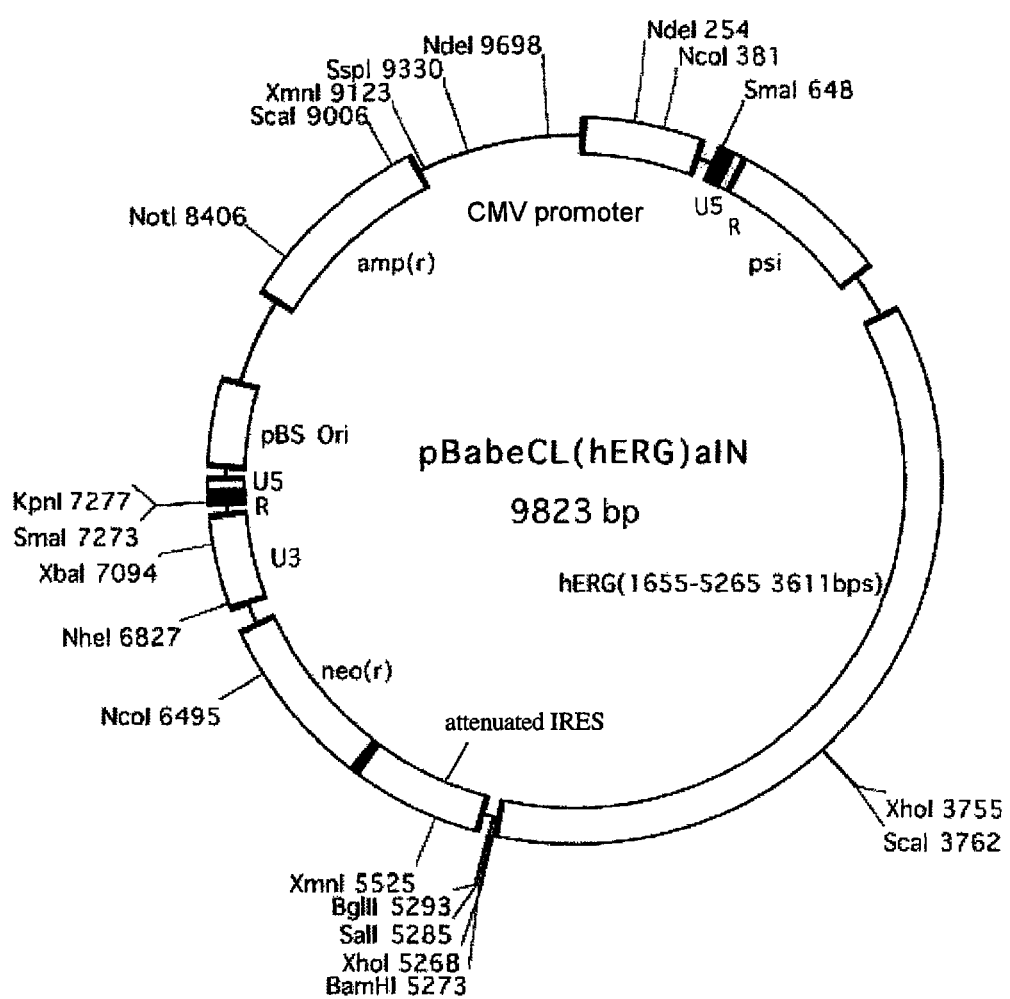
FIG. 7 shows the structure of a hERG gene-transferred retrovirus vector plasmid (pBabeCL(hERG)aIN).
Figure 8:
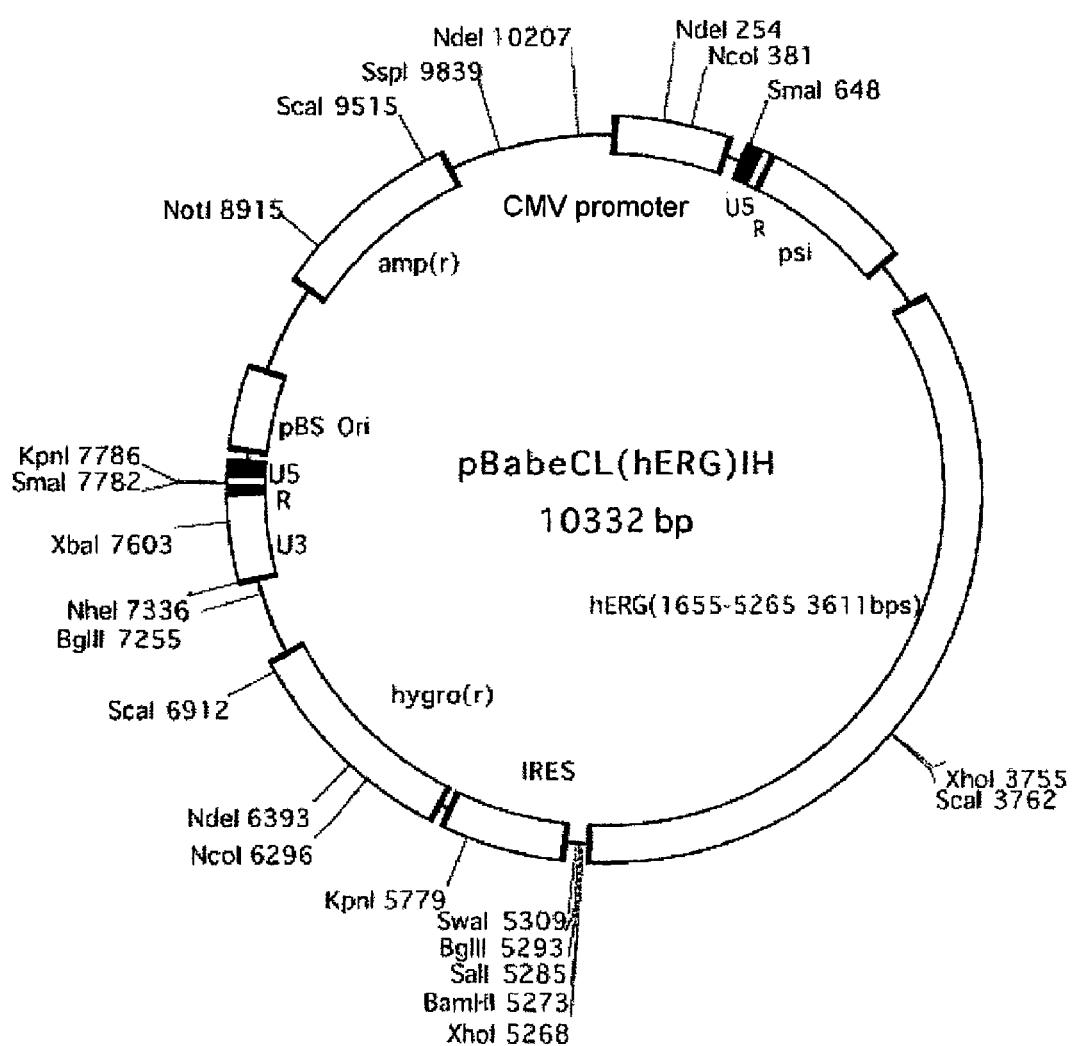
FIG. 8 shows the structure of a hERG gene-transferred retrovirus vector plasmid (pBabeCL(hERG)IH).
Figure 9:
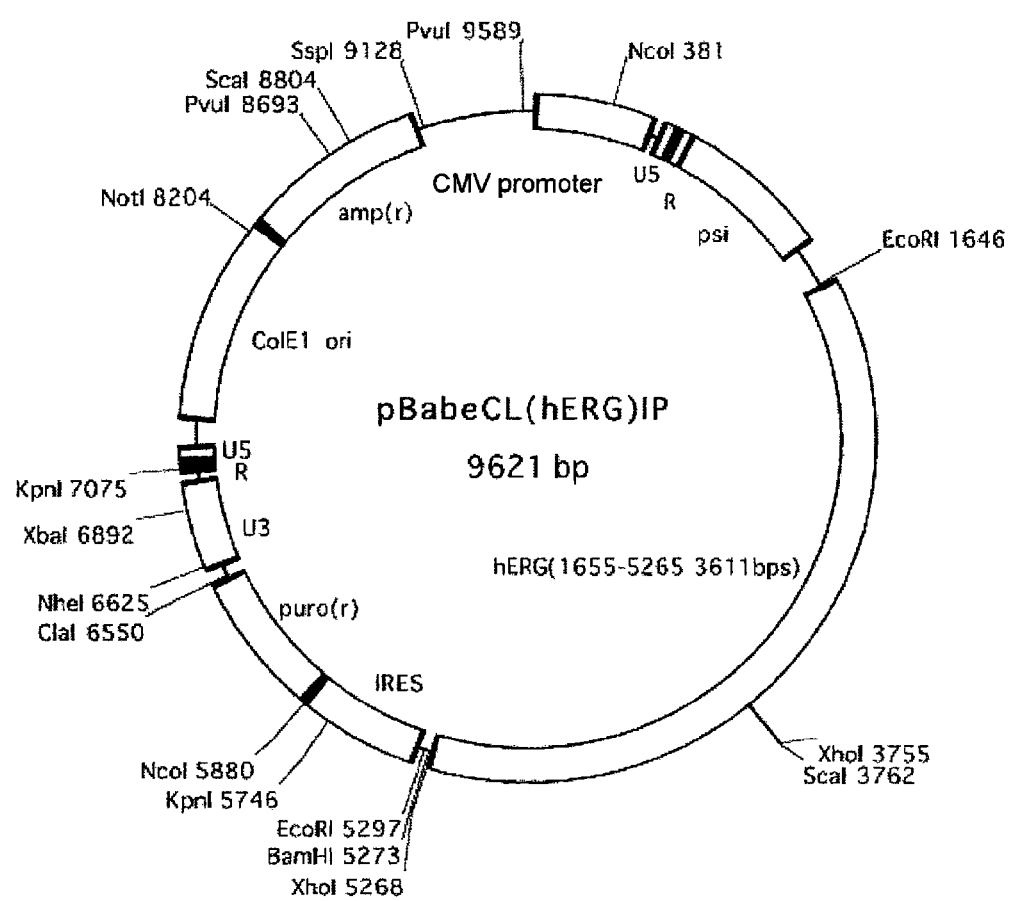
FIG. 9 shows the structure of a hERG gene-transferred retrovirus vector plasmid (pBabeCL(hERG)IP).
Figure 10:
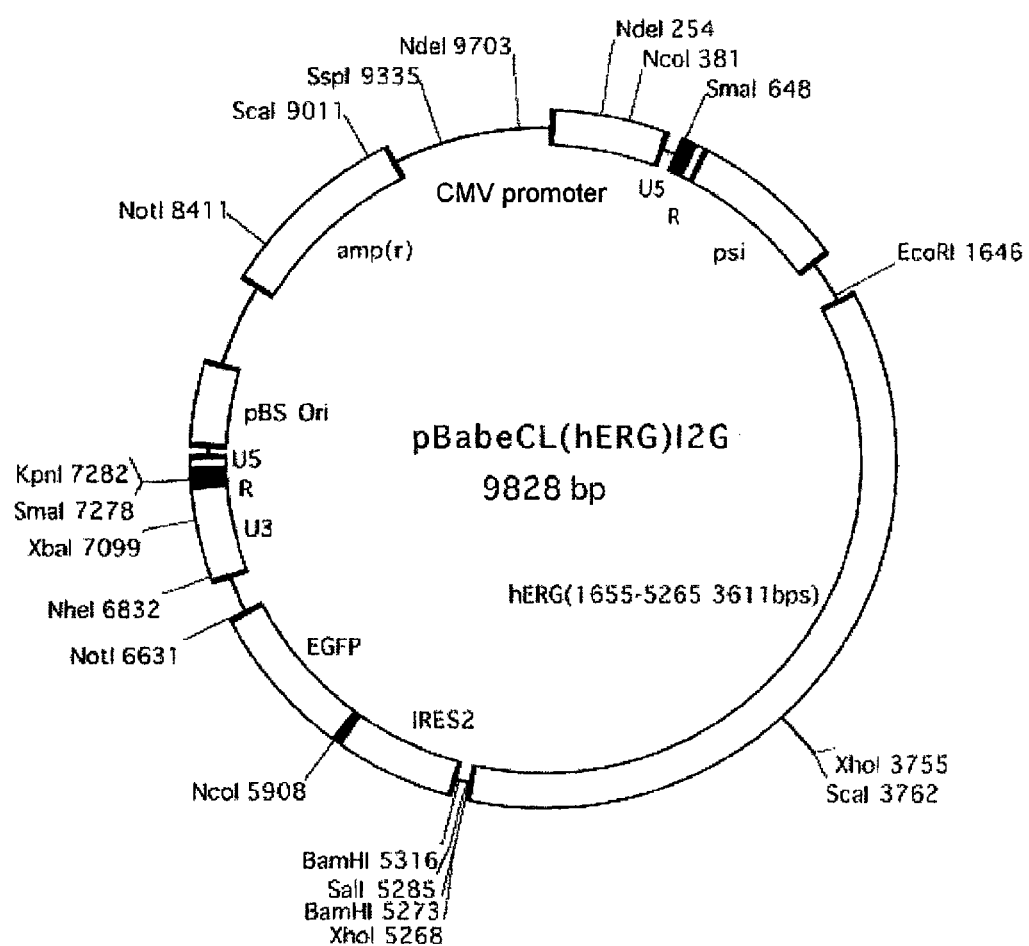
FIG. 10 shows the structure of a hERG gene-transferred retrovirus vector plasmid (pBabeCL(hERG)I2G).
Figure 11:
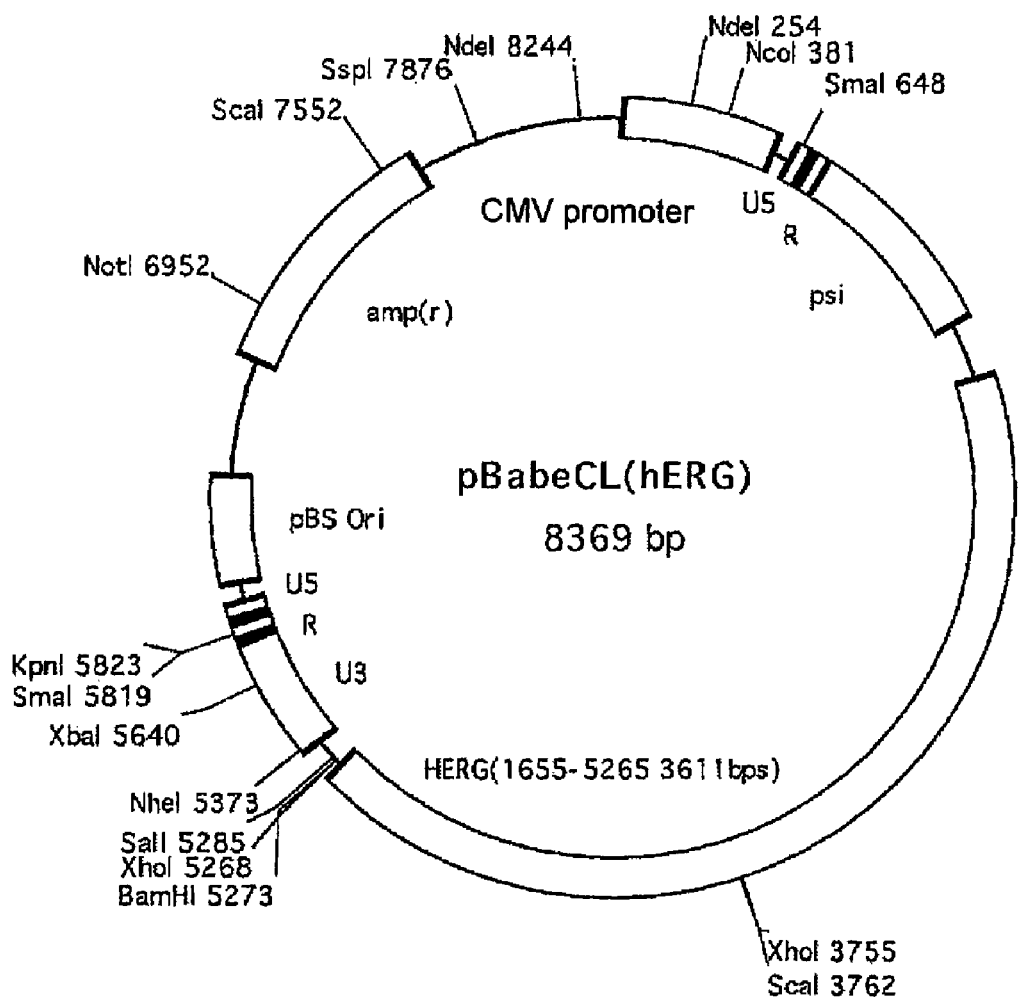
FIG. 11 shows the structure of a hERG gene-transferred retrovirus vector plasmid (pBabeCL(hERG)).

Preparation of Retrovirus Vector Plasmids for hERG Gene Transfer pBabeCLXaIN obtained in Example 2 was digested with restriction enzyme HpaI. Into this site, a hERG gene that had been cut out from pREP7hERG (obtained in Example 1) with KpnI and HindIII and then blunt-ended with T4 polymerase was inserted to thereby obtain pBabeCL(hERG)aIN (FIG. 7).

pBabeCLXIH obtained in Example 2 was digested with HpaI. Into this site, a hERG gene that had been cut out from pREP7hERG (obtained in Example 1) with KpnI and HindIII and then blunt-ended with T4 polymerase was inserted to thereby obtain pBabeCL(hERG)IH (FIG. 8).

pBabeCLXIP obtained in Example 2 was digested with HpaI. Into this site, a hERG gene that had been cut out from pREP7hERG (obtained in Example 1) with KpnI and HindIII and then blunt-ended with T4 polymerase was inserted to thereby obtain pBabeCL(hERG)IP (FIG. 9).

pBabeCLXI2G obtained in Example 2 was digested with HpaI. Into this site, a hERG gene that had been cut out from pREP7hERG (obtained in Example 1) with KpnI and HindIII and then blunt-ended with T4 polymerase was inserted to thereby obtain pBabeCL(hERG)I2G (FIG. 10).

pBabeCLXIH obtained in Example 2 was digested with BglII to remove IRES-hyg(r) and then blunt-ended with Klenow fragment. Into this site, a hERG gene that had been cut out from pREP7hERG (obtained in Example 1) with KpnI and HindIII and then blunt-ended with T4 polymerase was inserted to thereby obtain pBabeCL(hERG) (FIG. 11).

Example 4

Preparation of Lentivirus Vector Plasmids

In order to insert a multicloning site, oligo DNAs consisting of SEQ ID NO: 9 and 10 were prepared by Japan Bio Service (Asaka City, Saitama) upon request of the inventors. The nucleotide sequences of the oligo DNAs were as follows.

```
oligo DNA:
GATCCCCCGGGCTGCAGGAATTCGATATCGTTAACG  (SEQ ID NO: 9)
TCGACCTCGAGGGTAC oligo DNA:
CCTCGAGGTCGACGTTAACGATATCGAATTCCTGCA  (SEQ ID NO: 10)
GCCCGGGG
```

Figure 12:
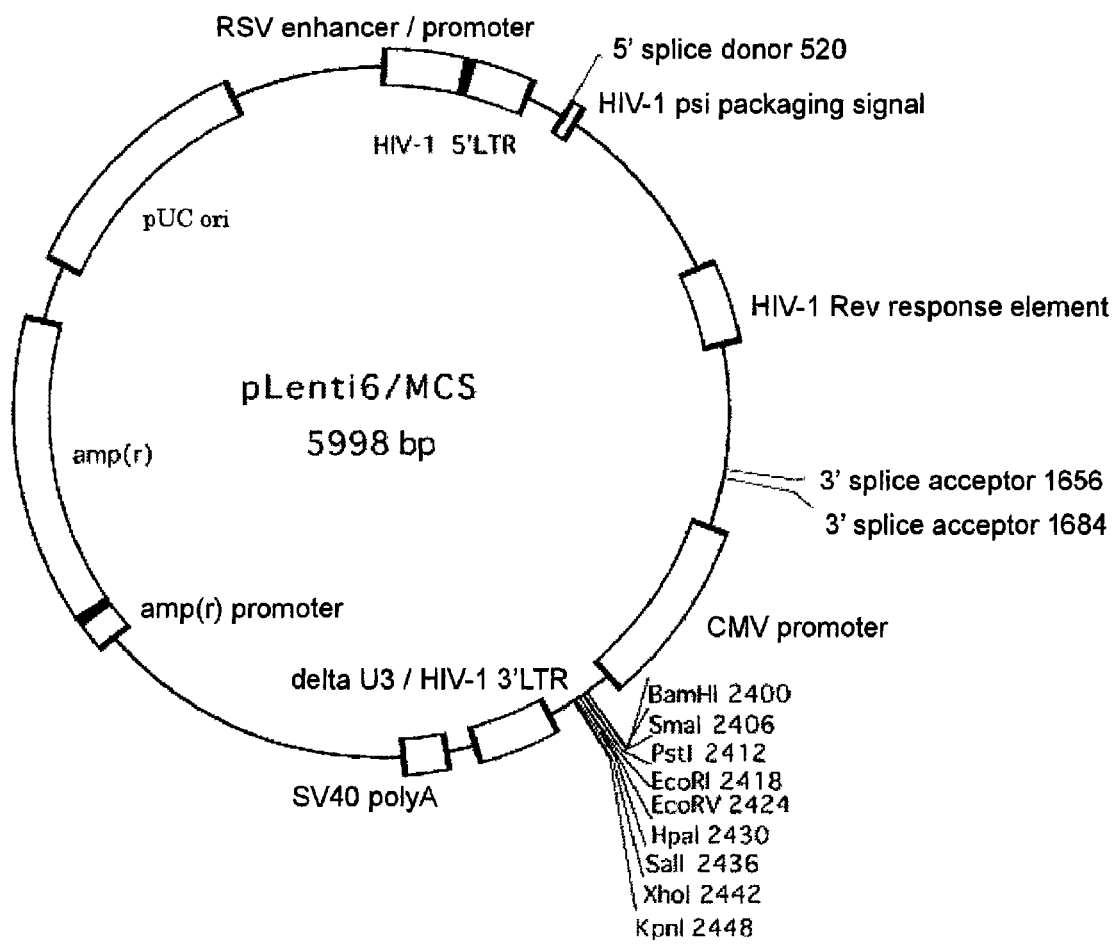
FIG. 12 shows the structure of a lentivirus vector plasmid (pLenti6/MCS).

The oligo DNAs of SEQ ID NO: 9 and 10 were annealed by thermally denaturing at 98° C. for 5 min and then slowly returning to room temperature.

pLenti6/V5-GW/lacZ (Invitrogen, Carlsbad, Calif., catalog #K4955-10) was digested with restriction enzymes BamHI and KpnI to remove lacZ-V5 epitope-SV40 early promoter-EM7 promoter-blasticidin(r). Into this site, the above-described oligo DNA was inserted to thereby obtain pLenti6/MCS (FIG. 12).

In order to introduce central polypurine tract (cPPT) for enhancing gene transfer ability, oligo DNA primers as shown in SEQ ID NO: 11 and 12 were prepared by Japan Bio Service (Asaka City, Saitama) upon request of the inventors with reference to a previously reported method (Zennou, V. Z. et al., Cell vol. 101 173-185 (2000)).

```
Primer:
GTCGTCATCGATACAAATGGCAGTATTATCC       (SEQ ID NO: 11)

Primer:
GTCGTCAAGCTTCCAAACTGGATCTCTGCTGTCC    (SEQ ID NO: 12)
```

Figure 13:
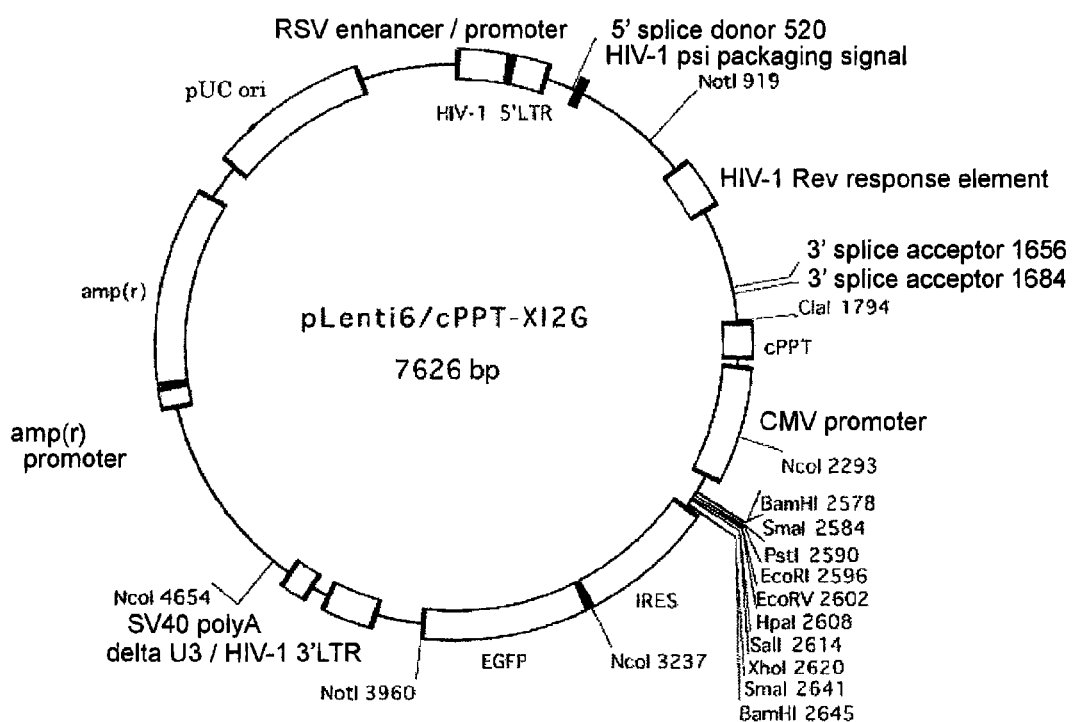
FIG. 13 shows the structure of a lentivirus vector plasmid (pLenti6/cPPT-XI2G).

By using the oligo DNAs consisting of SEQ ID NO: 11 and 12 as primers and plasmid pLP1 (ViraPower Lentiviral Gateway Expression kit, Invitrogen; K4960-00) as a template, PCR was performed with Expand High Fidelity PCR System (Roche Diagnostics, Mannheim, Germany). The thermal conditions were 30 cycles of 95° C. for 30 sec, 61° C. for 30 sec and 68° C. for 1 min. As a result, a DNA fragment of approx. 0.2 kb was obtained. This DNA fragment was inserted into pT7Blue (Novagen, Darmstadt, Germany, catalog #69967-3) to thereby obtain cPPT-pT7Blue. The nucleotide sequence of the DNA fragment was confirmed with ABI prism DNA sequencing kit (Perkin-Elmer Applied Biosystems, Foster City, Calif.) to be identical with the already reported sequence of cPPT (Zennou, V. Z. et al., Cell vol. 101 173-185 (2000)).

pBluescript (Stratagene) was digested with restriction enzymes ClaI and BamHI. Into this site, ClaI/HindIII-digested cPPT-pT7Blue containing cPPT and BamHI/HindIII-digested pLenti6/MCS containing CMV promoter was inserted to thereby obtain cPPT-CMV-pBS.

pLenti6/MCS was digested with ClaI and BamHI to remove CMV promoter. Into this site, ClaI/BamHI-digested cPPT-CMV-pBS containing cPPT-CMV promoter was inserted to thereby obtain pLenti6/cPPT-MCS, which was then digested with KpnI and blunt-ended with T4 polymerase. Into this site, IRES-EGFP fragment that had been cut out from pIRES2-EGFP (Clontech, catalog #6029-1) with HincII was inserted to thereby obtain pLenti6/cPPT-XI2G (FIG. 13).

Example 5

Figure 14:
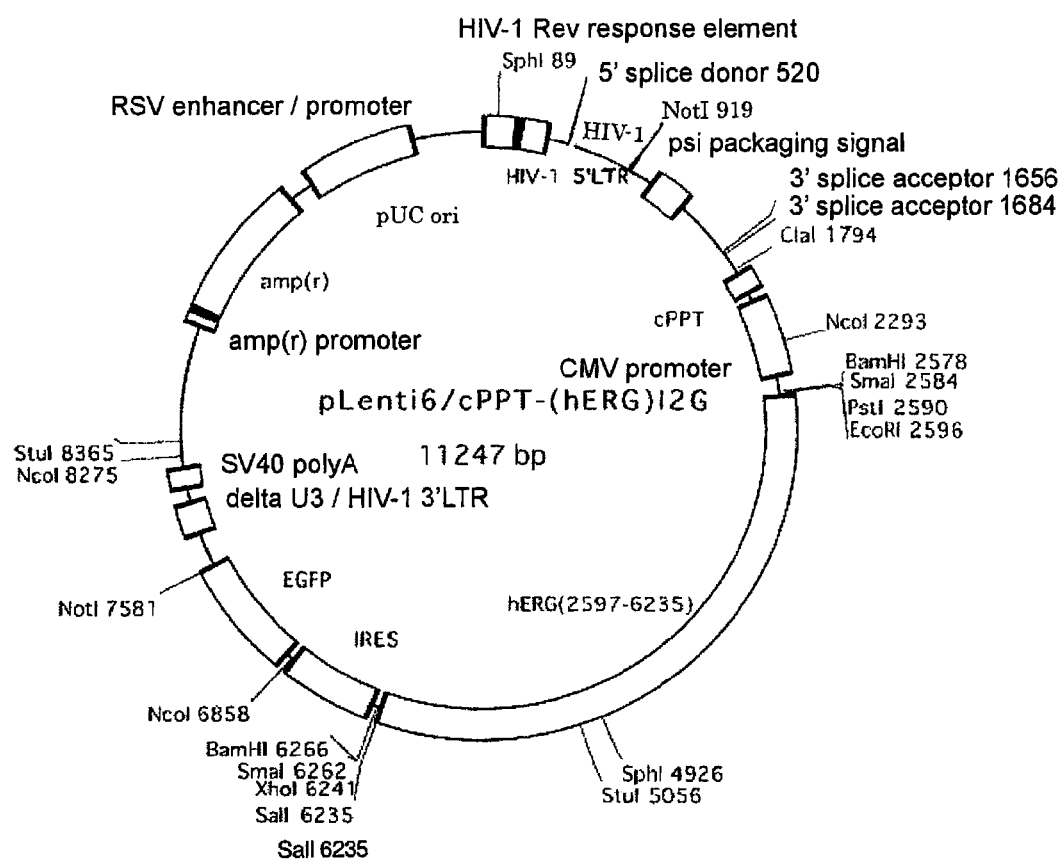
FIG. 14 shows the structure of a hERG gene-transferred lentivirus vector plasmid (pLenti6/cPPT-(hERG)I2G).

Preparation of Lentivirus Vector Plasmid for hERG Gene Transfer pLenti6/cPPT-XI2G obtained in Example 4 was digested with EcoRI and SalI. Into this site, a hERG gene that had been cut out from pBabeCL(hERG)I2G (obtained in Example 3) with EcoRI and SalI and then blunt-ended with T4 polymerase was inserted to thereby obtain pLenti6/cPPT-(hERG)I2G (FIG. 14).

Example 6

Preparation of Vector Plasmid pREP7BERG obtained in Example 1 was digested with KpnI and HindIII to cut out the hERG gene, which was inserted into KpnI/HindIII-digested pZeoSV2 (Invitrogen) to thereby obtain pZeohERG pZeohERG was introduced into a dam⁻ E. coli strain SCS110, which was then mass-cultured and subjected to plasmid preparation. SV40 promoter-hERG gene (ClaI/fill-in-HindIII) obtained from the resultant plasmid was introduced into a DNA fragment (NurI/HindIII digested product) that had been obtained from pcDNA3.1 Neo by removing CMV promoter to thereby prepare pSV hERG-Neo. The mass culture of the expression vector-introduced E. coli was conducted by conventional methods. The purification of the vector was conducted by using EndoFree Plasmid Kit (Qiagen).

Example 7

Preparation of Retrovirus Vector for hERG Gene Transfer

293-EBNA cells (Invitrogen, catalog #R620-07) ($2\times10^6$ cells) were cultured in 10 ml of DMEM (Sigma catalog #D5796)-10% fetal bovine serum (FCS)-penicillin/streptomycin (PS) (hereinafter, referred to as "EBNA culture medium") in 10 cm collagen-coated dishes (IWAKI, Tokyo, catalog #4020-010). Next day, 3.3 μg each of pV-gp (obtained from pVPack-GP (Stratagene, catalog #217566) by digesting with NsiI and XbaI to remove IRES-hisD, blunt-ending with T4 polymerase and then self-ligating), pVPack-VSV-G (Stratagene, catalog #217567) and pBabeCL(hERG)I2G obtained in Example 3 were transfected into the cells by using a lipofection reagent TransIT (Panvera, Madison, Wis., catalog #MIR2300). Six to twelve hours after the transfection, EBNA culture medium was exchanged and culture was continued at 37° C.

Two days after the transfection, the culture medium was recovered and centrifuged at 1,200 g for 10 min. The resultant supernatant was filtered through a 0.45 μm filter (Millipore, MILLEX-HV, catalog #SLHV025LS) to thereby obtain a non-concentrated retrovirus vector, which was used in subsequent experiments.

Example 8

Preparation of Lentivirus Vector for hERG Gene Transfer

293-EBNA cells (Invitrogen, catalog #R620-07) ($4\times10^6$ cells) were cultured in 10 ml of DMEM (Sigma, catalog #D5796)-10% fetal bovine serum (FCS)-penicillin/streptomycin (PS) (hereinafter, referred to as "EBNA culture medium") in 10 cm collagen-coated dishes (IWAKI, Tokyo, catalog #4020-010). Next day, 2.5 μg each of pLP1, pLP2, pLP/VSVG (all from Invitrogen, catalog #K4970-10) and the lentivirus vector plasmid for human hERG gene transfer obtained in Example 5 were transfected into the cells by using a lipofection reagent TransIT (Panvera, Madison, Wis., catalog #MIR2300). Six to twelve hours after the transfection, EBNA culture medium was exchanged and culture was continued at 37° C.

Two days after the transfection, the culture medium was recovered and centrifuged at 1,200 g for 10 min. The resultant supernatant was filtered through a 0.45 μM filter (Millipore, MILLEX-HV, catalog #SLHV025LS) to thereby obtain a non-concentrated lentivirus vector, which was used in subsequent experiments.

Example 9

Concentration of the Retrovirus Vector

The virus vector prepared in Example 7 was concentrated as described below. Ultracentifuge tubes (50 Ultra-Clear Tubes, Beckman, Palo Alto, Calif., catalog #344058) were sterilized with 70% ethanol and rinsed with distilled water. Into each tube, approx. 35 ml of the non-concentrated virus vector was transferred. The tubes were placed in SW28 ultracentrifuge rotor (Beckman) and centrifuged at 19,500 rpm for 100 min using ultracentrifuge equipment XL-90 (Beckman). After the centrifugation, the supernatant was discarded and each tube was left in ice. After one hour, a concentrated virus vector solution was obtained in a form of approx. 100 μl of culture remaining on the tube wall. If necessary, concentrated virus vector solutions were collected and subjected to ultracentrifugation again to thereby prepare a re-concentrated virus vector solution.

Example 10

Concentration of the Lentivirus Vector

The virus vector prepared in Example 8 was concentrated as described below. Ultracentifuge tubes (50 Ultra-Clear Tubes, Beckman, Palo Alto, Calif., catalog #344058) were sterilized with 70% ethanol and rinsed with distilled water. Into each tube, approx. 35 ml of the non-concentrated virus vector was transferred. The tubes were placed in SW28 ultracentrifuge rotor (Beckman) and centrifuged at 19,500 rpm for 100 min using ultracentrifuge equipment XL-90 (Beckman). After the centrifugation, the supernatant was discarded and each tube was left in ice. After one hour, a concentrated virus vector solution was obtained in a form of approx. 100 µl of culture remaining on the tube wall. If necessary, concentrated virus vector solutions were collected and subjected to ultracentrifugation again to thereby prepare a re-concentrated virus vector solution.

Example 11

Preparation of hERG-Expressing Cells with Retrovirus Vector for hERG Gene Transfer (1)

hERG gene transfer into cell with the virus vector prepared in Example 7 was performed as described below.

Briefly, Chinese Hamster Ovary (CHO)-K1 cells (Cell Bank, RIKEN Gene Bank) ($3 \times 10^3$ cells) were cultured in 100 µl of DMEM/F12 (Invitrogen Corp., catalog #11320-033)-10% fetal bovine serum (FCS)-penicillin/streptomycin (PS) (hereinafter, referred to as "CHO culture medium") in 96 well plates (Becton-Dickinson, Franklin Lakes, N.J. catalog #35-3075). The next day, 100 µl of the virus vector prepared in Example 7 was added to the CHO cells together with polybrene (final concentration: 8 µg/ml) (Sigma H9268; also known as hexadimethrine bromide) diluted with the culture medium. The next day, the culture medium containing the virus vector was exchanged with 200 µl of the CHO culture medium. The culture was continued for another three days. The resultant hERG gene-transferred cells were subjected to the following experiments to know rough natures of them as a cell population. If necessary, the cells were subjected to the cell cloning as described later in Example 18, before use in the following experiments.

Example 12

Preparation of hERG-Expressing Cells with Lentivirus Vector for hERG Gene Transfer (2)

hERG gene transfer into cell with the virus vector prepared in Example 8 was performed as described below.

Briefly, Chinese Hamster Ovary (CHO)-K1 cells (Cell Bank, RIKEN Gene Bank) ($3 \times 10^3$ cells) were cultured in 100 µl of DMEM/F12 (Invitrogen Corp., catalog #11320-033)-10% fetal bovine serum (FCS)-penicillin/streptomycin (PS) (hereinafter, referred to as "CHO culture medium") in 96 well plates (Becton-Dickinson, Franklin Lakes, N.J., catalog #35-3075). The next day, 100 µl of the virus vector prepared in Example 8 was added to the CHO cells together with polybrene (final concentration: 8 µg/ml) (Sigma H9268; also known as hexadimethrine bromide) diluted with the culture medium. The next day, the culture medium containing the virus vector was exchanged with 200 µl of the CHO culture medium. The culture was continued for another three days. The resultant hERG gene-transferred cells were subjected to the following experiments to know rough natures of them as a cell population. If necessary, the cells were subjected to the cell cloning as described later in Examples 17 and 18, before use in the following experiments.

Example 13

Preparation of hERG-Expressing Cells with Retrovirus Vector for hERG Gene Transfer (2)

hERG gene transfer into cell with the centrifuge-concentrated virus vector from Example 9 was performed as described below.

Briefly, Chinese Hamster Ovary (CHO)-K1 cells (Cell Bank, RIKEN Gene Bank) ($3 \times 10^3$ cells) were cultured in 100 µl of DMEM/F12 (Invitrogen Corp., catalog #11320-033)-10% fetal bovine serum (FCS)-penicillin/streptomycin (PS) (hereinafter, referred to as "CHO culture medium") in 96 well plates (Becton-Dickinson, Franklin Lakes, N.J., catalog #35-3075). The next day, 100 µl of the centrifuge-concentrated virus vector from Example 9 was added to the CHO cells together with polybrene (final concentration: 8 µg/ml) (Sigma H9268; also known as hexadimethrine bromide) diluted with the culture medium. The next day, the culture medium containing the virus vector was exchanged with 200 µl of the CHO culture medium. The culture was continued for another three days. The resultant hERG gene-transferred cells were subjected to the following experiments to know rough natures of them as a cell population. If necessary, the cells were subjected to the cell cloning as described later in Example 18, before use in the following experiments.

Example 14

Preparation of hERG-Expressing Cells with Retrovirus Vector for hERG Gene Transfer (3)

The cell cloning described in Example 18 was performed to select a cell strain in which an appropriate hERG current could be recorded. hERG gene was transferred into the resultant cell strain with the centrifuge-concentrated virus vector from Example 9 as described below.

A hERG-expressing cell strain ($3 \times 10^3$ cells) obtained in Example 13 was cultured in 100 µl of DMEM/F12 (Invitrogen Corp., catalog #11320-033)-10% fetal bovine serum (FCS)-penicillin/streptomycin (PS) (hereinafter, referred to as "CHO culture medium") in 96 well plates (Becton-Dickinson, Franklin Lakes, N.J., catalog #35-3075). The next day, 100 µl of the centrifuge-concentrated virus vector from Example 9 was added to the CHO cells to give a final concentration of 8 µg/ml, together with polybrene (final concentration: 8 µg/ml) (Sigma H9268; also known as hexadimethrine bromide) diluted with the culture medium. The next day, the culture medium containing the virus vector was exchanged with 200 µl of the CHO culture medium. The culture was continued for another three days. The resultant hERG gene-transferred cells were subjected to the following experiments to know rough natures of them as a cell population. If necessary, the cells were subjected to the cell cloning as described later in Example 18, before use in the following experiments.

Example 15

Preparation of hERG-Expressing Cells with Lentivirus Vector for hERG Gene Transfer (2)

hERG gene transfer into cell with the virus vector prepared in Example 10 was performed as described below.

Briefly, Chinese Hamster Ovary (CHO)-K1 cells (Cell Bank, RIKEN Gene Bank) ($3\times10^3$ cells) were cultured in 100 μl of DMEM/F12 (Invitrogen Corp., catalog #11320-033)-10% fetal bovine serum (FCS)-penicillin/streptomycin (PS) (hereinafter, referred to as "CHO culture medium") in 96 well plates (Becton-Dickinson, Franklin Lakes, N.J., catalog #35-3075). The next day, 100 μl of the centrifuge-concentrated virus vector from Example 10 was added to the CHO cells together with polybrene (final concentration: 8 μg/ml) (Sigma H9268; also known as hexadimethrine bromide) diluted with the culture medium. The next day, the culture medium containing the virus vector was exchanged with 200 μl of the CHO culture medium. The culture was continued for another three days. The resultant hERG gene-transferred cells were subjected to the following experiments to know rough natures of them as a cell population. If necessary, the cells were subjected to the cell cloning as described later in Examples 17 and 18, before use in the following experiments.

Example 16

Preparation of hERG-Expressing Cells by Lipofection with hERG Gene Transfer Vector hERG gene transfer vector was introduced into CHO-K1 cells (Cell Bank, Riken Gene Bank) as described below in accordance with Effectene Transfection Reagent Handbook.

To a 2-day culture of the CHO-K1 cells in culture dishes 6 cm in diameter were added approx. 1 μg of hERG expression vector (SV-hERG-neo) dissolved in TE solution and 8 μl of enhancer which were mixed to give a final volume of 150 μl and agitated for approx. 1 sec, and left stationary for 2-5 min at room temperature. Subsequently, 25 μl of Effectene Transfection Reagent was added thereto. The mixture was agitated for approx. 10 sec and left stationary for 5-10 min at room temperature. Then, 1 ml of the medium was added thereto. The cells were washed with PBS(−), transferred into a culture dish containing 4 ml of medium, and cultured in an incubator at 37° C. under 5% $CO_2$. The next day, cells were taken off from the culture dish with trypsin and suspended in a medium containing G418 that is 500 μg in potency. After several days of culture, cells were subjected to the cell cloning as described in Example 18 before use in the following experiments.

Example 17

Isolation and Concentration of hERG High Expressing Cells by FACS with GFP Expression as an Indicator From the hERG-transferred cells prepared in Example 12 or 15, those cells that express hERG still higher were isolated and concentrated by using FACSAria (Becton Dickinson) with GFP expression as an indicator. Briefly, cells prepared in 10 cm dishes were taken off with trypsin, and GFP high expressing cells alone were isolated according to the protocol of FACSAria and analyzed. The results of analysis revealed that GFP high expressing cells were concentrated. The resultant cells were subjected to the cell cloning as described in Example 18 before use in the following experiments.

Example 18

Cloning of hERG Channel-Expressing Cells

The cloning of cells was performed by the limiting dilution culture method. A cell suspension was prepared so that each well of 96-well culture plates contained 0.3 cells. A 200 μl aliquot of the cell suspension was dispensed into each well. About two weeks later, under microscopic observation, cells of those wells where a single cell population (colony) was observed in a single well were transferred into 24-well culture plates and cultured further. Thereafter, the scale of culture was expanded to F75 culture flask. From the resultant cells, hERG channel-expressing cell strains were selected by Western blotting to confirm protein expression and electrophysiological techniques to confirm functional expression of hERG channel (Examples 19 and 20).

Example 19

Detection of hERG Channel by Western Blotting

This experiment was conducted by using CHO-K1 cells, the cell strain into which hERG gene was transferred by lipofection (Example 16) and the cell strain into which hERG gene was transferred with retrovirus (Example 14). Individual cells cultured in 6-well plates were washed with ice-cooled PBS. Then, a lysis buffer (150 mmol/L NaCl, 50 mmol/L Tris-HCl (pH 7.5), 5 mmol/L EDTA, 0.5% Nonidet R P-40, 0.5% deoxycholic acid sodium) supplemented with Protease Inhibitor Cocktail (SIGMA-Aldrich Co.) was added thereto, and the cells were scraped off with a cell scraper. The resultant cells were collected in Eppendorf tubes and centrifuged at 4° C. at 10,000 rpm (centrifuge: MRX-152, rotor: TMA-6; TOMY SEIKO) for 3 min. The resultant supernatants were recovered as samples. Protein concentrations in samples were determined with BCA Protein Assay Kit (Pierce Biotechnology Inc., Rockford, Ill., USA).

Electrophoresis and transfer of proteins were examined with NOVEX (Invitrogen) apparatuses. Briefly, appropriate amounts of NuPAGE LDS Sample Buffer (Invitrogen) and NuPAGE Sample Reducing Agent (Invitrogen) were added to the recovered sample and heated at 95° C. for 3 min. The resultant sample was applied to NuPAGE 3-8% Tris-Acetate Gel (Invitrogen) and electrophoresed at 120V for about one hour using NuPAGE Tris-Acetate Running Buffer (Invitrogen). The resultant gel was mounted in Xcell Surelock™ (Invitrogen) together with Immun-Blot PVDF Membrane (Bio-Rad Laboratories, Inc.) and transferred at 30V for about one hour by using NuPAGE Transfer Buffer (Invitrogen).

Anti-hERG (Alomone Labs) was used as a primary antibody, and anti-rabbit IgG HRP-linked antibody (Cell Signaling Technology, Inc.) was used as a secondary antibody After primary antibody reaction and secondary antibody reaction, the PVDF Membrane was washed with 0.1% Tween20/PBS. Detection of bound antibody was performed with ECL detection kit (Amersham Biosciences Corp.).

Figure 15:
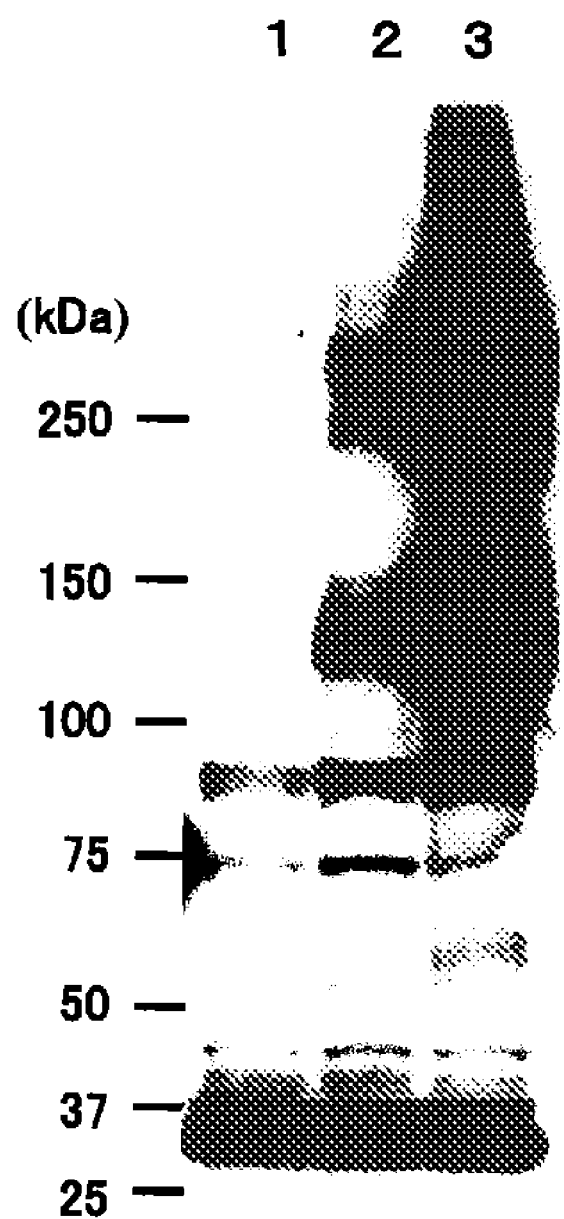
FIG. 15 shows the results of detection of hERG channel protein by Western blotting. (Lane 1: normal CHO-K1 cells; Lane 2: cell strain into which hERG gene was transferred by lipofection; Lane 3: cell strain into which hERG gene was transferred with retrovirus).

As a result, a band of a molecular weight of approx. 150 kD corresponding to the hERG protein was not detected in normal CHO-K1 cells (FIG. 15, lane 1). A weak band of the hERG protein was detected in cell strain M3 which was established by hERG gene transfer by lipofection (FIG. 15, lane 2). In contrast, a large amount of the hERG protein was detected clearly in the cell strain into which hERG gene was transferred with retrovirus (FIG. 15, lane 3).

Briefly, hERG currents were induced by changing the potential from −80 mV to +20 mV for 1 sec and then to −50 mV for 1 sec. The peak value of the tail current observed when the potential was restored to −50 mV was taken as the amplitude of hERG current. The distributions of hERG currents recorded in the cell strain into which hERG gene was transferred by lipofection and the cell strains into which hERG gene was transferred with retrovirus are shown in FIG. 16 and Table 1.

Figure 16:
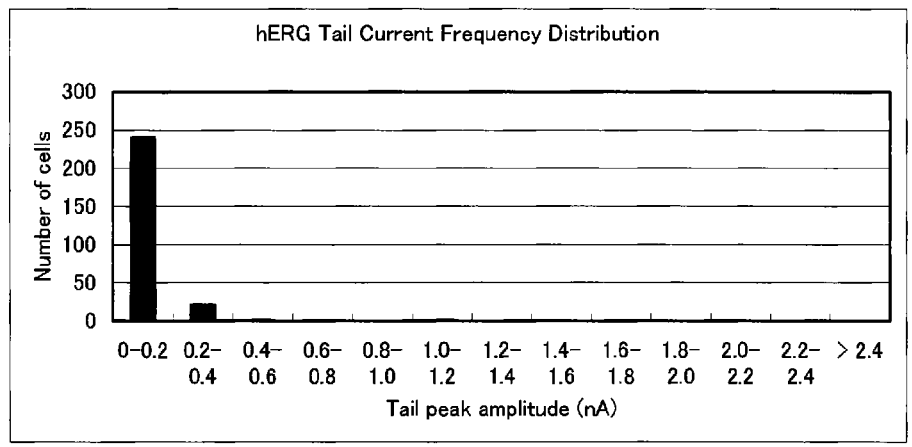
FIG. 16 shows the distribution of hERG currents. (A: cell strain into which hERG gene was transferred by lipofection; B: cell into which hERG gene was transferred with retrovirus; C: cell strain into which hERG gene was transferred with retrovirus).
Figure 16:
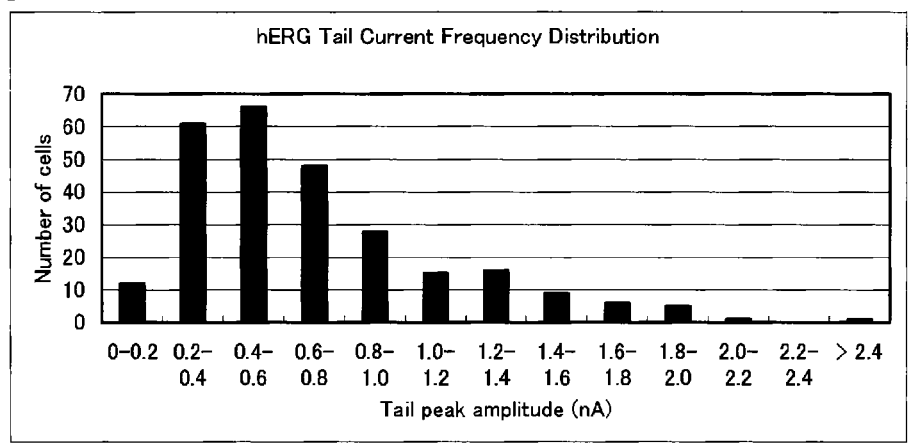
Figure 16:
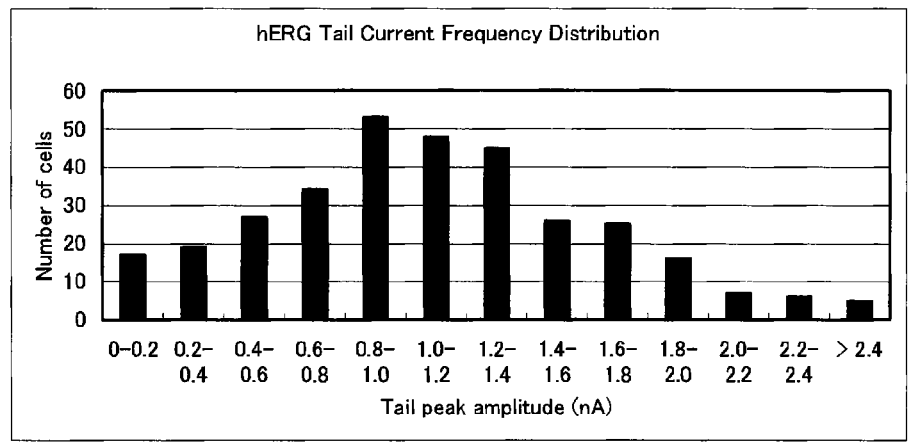

The hERG current distribution in the cell which was established by hERG gene transfer with retrovirus (Example 13) (Panel B of Table 1 and FIG. 16) was larger than that in the cell strain which was established by hERG gene transfer by lipofection (Example 16) (Panel A of Table 1 and FIG. 16), and the hERG current distribution in the cell strain (Example 14) was definitely still larger (Panel C of Table 1 and FIG. 16).

TABLE 1

| | Amplitude (nA) | | | | | | | | | | | | | |
|---|---|---|---|---|---|---|---|---|---|---|---|---|---|---|
| | 0-0.2 | 0.2-0.4 | 0.4-0.6 | 0.6-0.8 | 0.8-1.0 | 1.0-1.2 | 1.2-1.4 | 1.4-1.6 | 1.6-1.8 | 1.8-2.0 | 2.0-2.2 | 2.2-2.4 | >2.4 | SUM |
| A | | | | | | | | | | | | | | |
| number | 240 | 21 | 1 | 1 | 0 | 1 | 0 | 0 | 0 | 0 | 0 | 0 | 0 | 264 |
| ratio (%) | 90.9 | 8.0 | 0.4 | 0.4 | 0.0 | 0.4 | 0.0 | 0.0 | 0.0 | 0.0 | 0.0 | 0.0 | 0.0 | 100.0 |
| B | | | | | | | | | | | | | | |
| number | 12 | 61 | 66 | 48 | 28 | 15 | 16 | 9 | 6 | 5 | 1 | 0 | 1 | 268 |
| ratio (%) | 4.5 | 22.8 | 24.6 | 17.9 | 10.4 | 5.6 | 6.0 | 3.4 | 2.2 | 1.9 | 0.4 | 0.0 | 0.4 | 100.0 |
| C | | | | | | | | | | | | | | |
| number | 17 | 19 | 27 | 34 | 53 | 48 | 45 | 26 | 25 | 16 | 7 | 6 | 5 | 328 |
| ratio (%) | 5.2 | 5.8 | 8.2 | 10.4 | 16.2 | 14.6 | 13.7 | 7.9 | 7.6 | 4.9 | 2.1 | 1.8 | 1.5 | 100.0 |

Example 20

Measurement of hERG Current with Fully Automated High Throughput Patch Clamp System and Comparison of Current Distribution This experiment was conducted by using the cell strain into which hERG gene was transferred by lipofection (Example 16) and the cell (Example 13) and the cell strain (Example 14) into each of which hERG gene was transferred with retrovirus. hERG channel-expressing cells were cultured in F75 culture flasks. Then, cells were taken off from the F75 culture flasks with EDTA-containing PBS(−) solution and suspended in PBS solution to give an appropriate concentration (1.0-1.5×10$^6$ cells/ml). The cell suspension was transferred into a cell reserver in IonWorks HT™ system. Procedures for measuring hERG currents were as follows. First, PBS was dispensed into each well of measuring plates (PatchPlate™, Molecular Devices Corp.). Then, the cell suspension was dispensed into each well and left until cells formed a seal in a hole at the center of each well. After seal formation, an amphotericin B-containing solution (KCl 140 nm, MgCl$_2$ 1 mM, EGTA 1 mM, HEPES 20 mM, pH 7.25-7.3) was perfused to allow formation of a perforated patch. After perforated patch formation, potential changes were given to cells by the voltage clamp method through stimulation electrodes to induce hERG currents, followed by recording the hERG currents.

In Table 1, A, B and C represent hERG current distributions in the cell strain into which hERG gene was transferred by lipofection, the cell into which hERG gene was transferred with retrovirus, and the cell strain into which hERG gene was transferred with retrovirus, respectively.

Further, in order to evaluate the hERG current inhibitory activities of compounds more stably, cut-off values were set, followed by analysis of hERG currents in individual hERG-expressing cells. As for cut-off values, (1) the ratio of the peak value of the tail current to the value of current when depolarized to +20 mV that is less than 0.8; and (2) seal resistance that is less than 30 MΩ were set. Data satisfying these conditions were analyzed.

Figure 17:
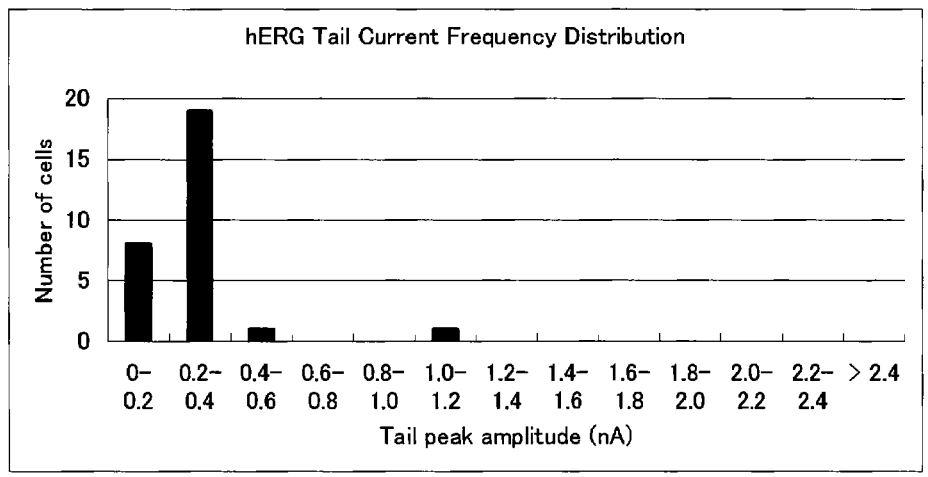
FIG. 17 shows the distribution of hERG currents analyzed with cut-off values. (A: cell strain into which HERO gene was transferred by lipofection; B: cell into which hERG gene was transferred with retrovirus; C: cell strain into which hERG gene was transferred with retrovirus; D: cell strain into which hERG gene was transferred with retrovirus and then cultured for one year continuously; E: cell strain into which hERG gene was transferred with lentivirus.)
Figure 17:
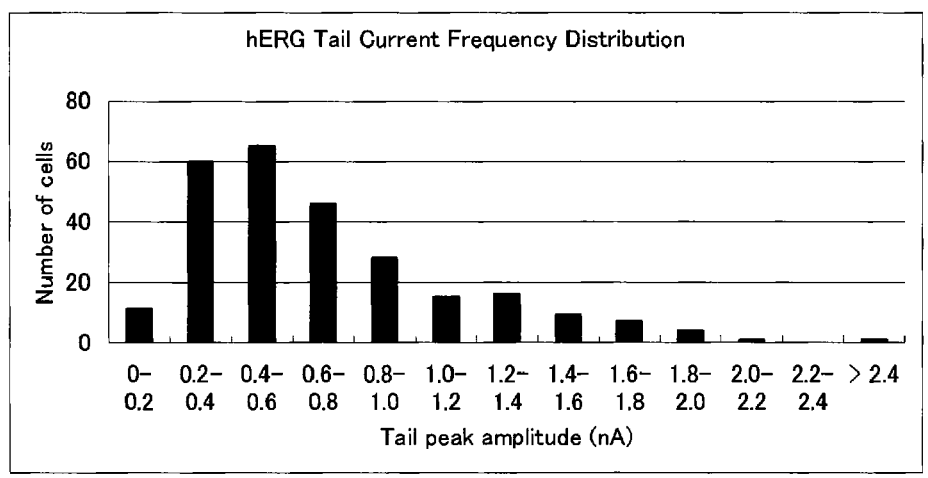
Figure 17:
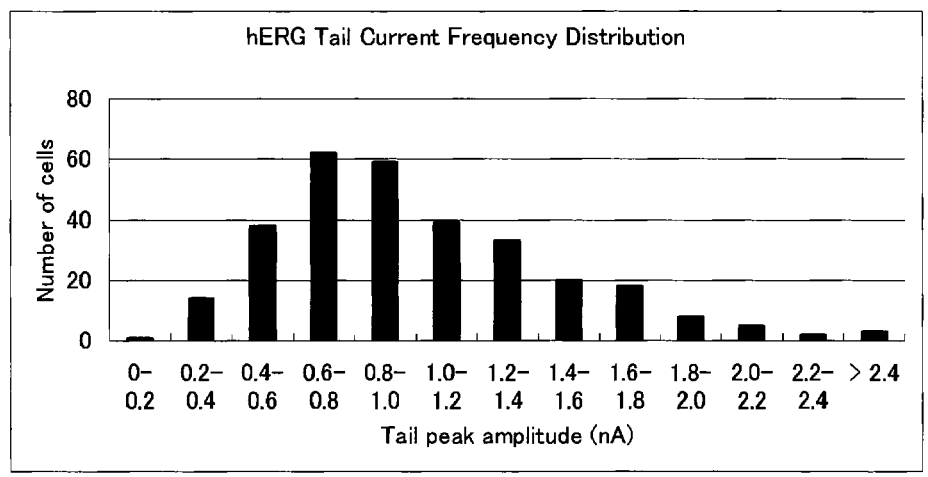
Figure 17:
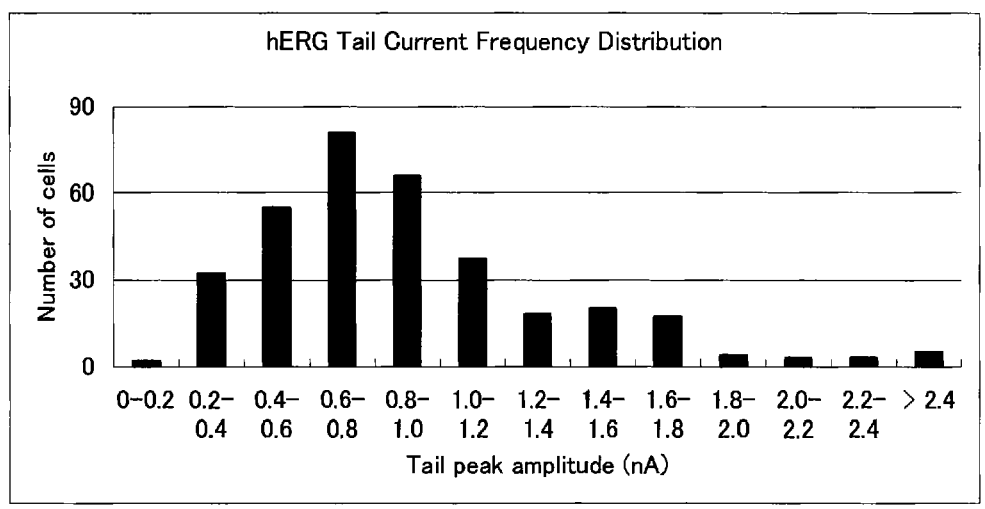
Figure 17:
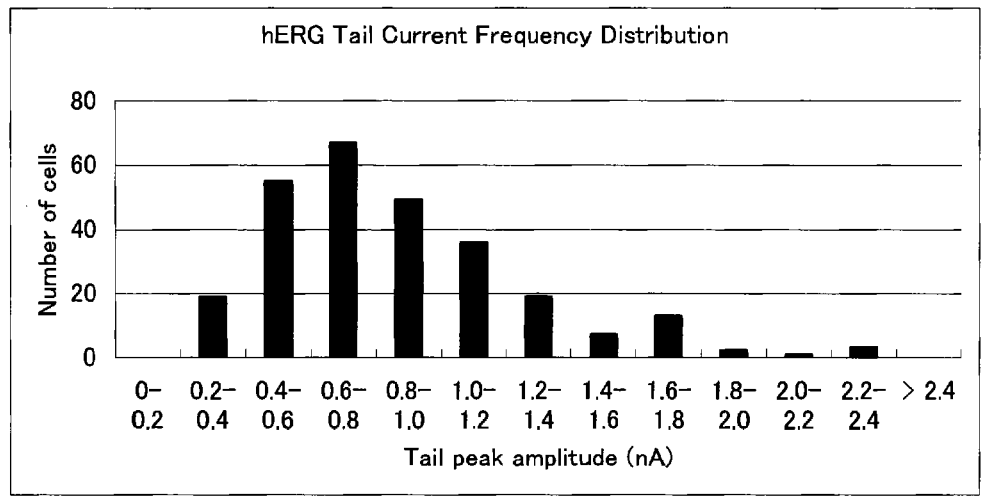

The results of analysis with the cut-off values are shown in FIG. 17 and Table 2.

The hERG current distribution in the cell which was established by hERG gene transfer with retrovirus (Example 13) (Panel B of Table 2 and FIG. 17) was larger than that in the cell strain which was established by hERG gene transfer by lipofection (Example 16) (Panel A of Table 2 and FIG. 17), and the hERG current distribution in the cell strain (Example 14) (Panel C of Table 2 and FIG. 17) was definitely still larger. Further, the hERG current in the cell which had been cultured continuously for one year was stable (Panel D of Table 2 and FIG. 17). Besides, the hERG current distribution in the cell strain that was established by hERG gene transfer with lentivirus was also definitely as large as that seen in the cell strain established with retrovirus. This meant that hERG channels are expressed stably even after one year continuous cultivation (Panel E of Table 2 and FIG. 17).

TABLE 2

| | Amplitude (nA) | | | | | | | | | | | | | |
|---|---|---|---|---|---|---|---|---|---|---|---|---|---|---|
| | 0-0.2 | 0.2-0.4 | 0.4-0.6 | 0.6-0.8 | 0.8-1.0 | 1.0-1.2 | 1.2-1.4 | 1.4-1.6 | 1.6-1.8 | 1.8-2.0 | 2.0-2.2 | 2.2-2.4 | >2.4 | SUM |
| A | | | | | | | | | | | | | | |
| number | 8 | 19 | 1 | 0 | 0 | 1 | 0 | 0 | 0 | 0 | 0 | 0 | 0 | 29 |
| ratio (%) | 27.6 | 65.5 | 3.4 | 0.0 | 0.0 | 3.4 | 0.0 | 0.0 | 0.0 | 0.0 | 0.0 | 0.0 | 0.0 | 100.0 |
| B | | | | | | | | | | | | | | |
| number | 11 | 60 | 65 | 46 | 28 | 15 | 16 | 9 | 7 | 4 | 1 | 0 | 1 | 263 |
| ratio (%) | 4.2 | 22.8 | 24.7 | 17.5 | 10.6 | 5.7 | 6.1 | 3.4 | 2.7 | 1.5 | 0.4 | 0.0 | 0.4 | 100.0 |
| C | | | | | | | | | | | | | | |
| number | 1 | 14 | 38 | 62 | 59 | 39 | 33 | 20 | 18 | 8 | 5 | 2 | 3 | 302 |
| ratio (%) | 0.3 | 4.6 | 12.6 | 20.5 | 19.5 | 12.9 | 10.9 | 6.6 | 6.0 | 2.6 | 1.7 | 0.7 | 1.0 | 100.0 |
| D | | | | | | | | | | | | | | |
| number | 2 | 32 | 55 | 81 | 66 | 37 | 18 | 20 | 17 | 4 | 3 | 3 | 5 | 343 |
| ratio (%) | 0.6 | 9.3 | 16.0 | 23.6 | 19.2 | 10.8 | 5.2 | 5.8 | 5.0 | 1.2 | 0.9 | 0.9 | 1.5 | 100.0 |
| E | | | | | | | | | | | | | | |
| number | 0 | 19 | 55 | 67 | 49 | 36 | 19 | 7 | 13 | 2 | 1 | 3 | 0 | 271 |
| ratio (%) | 0.0 | 7.0 | 20.3 | 24.7 | 18.1 | 13.3 | 7.0 | 2.6 | 4.8 | 0.7 | 0.4 | 1.1 | 0.0 | 100.0 |

In Table 2, A, B, C, D and E represent hERG current distributions in the cell strain into which hERG gene was transferred by lipofection, the cell into which hERG gene was transferred with retrovirus, the cell strain into which hERG gene was transferred with retrovirus, the cell strain into which hERG gene was transferred with retrovirus and then cultured for one year continuously, and the cell strain into which hERG gene was transferred with lentivirus, respectively.

Example 21

Evaluation of the hERG Channel Inhibitory Activities of Test Compounds with Fully Automated High Throughput Patch Clamp System This experiment was conducted by using the cell strain into which hERG gene was transferred by lipofection (Example 16) and the cell strain into which hERG gene was transferred with retrovirus (Example 14). hERG currents were measured in the same manner as described in Example 20. With respect to the inhibitory activities of test compounds or known compounds against hERG channels, inhibition ratios were calculated from the ratios of the peak value of the tail current after the addition of various concentrations of test compounds, taking the peak value of the tail current recorded before the addition of the relevant test compound as 100%. From the inhibition ratios of test compounds at individual concentrations, hERG current inhibitory activity values ($IC_{50}$) were calculated.

Each drug was evaluated at the following concentrations: 0.016, 0.048, 0.014, 0.041, 0.123, 0.37, 1.11 and 3.33 µM for astemizole, E-4031, risperidone and verapamil; and 0.048, 0.014, 0.041, 0.123, 0.37, 1.11, 3.33 and 10 µM for quinidine. The drugs were allowed to act for about 4 min.

Figure 18:
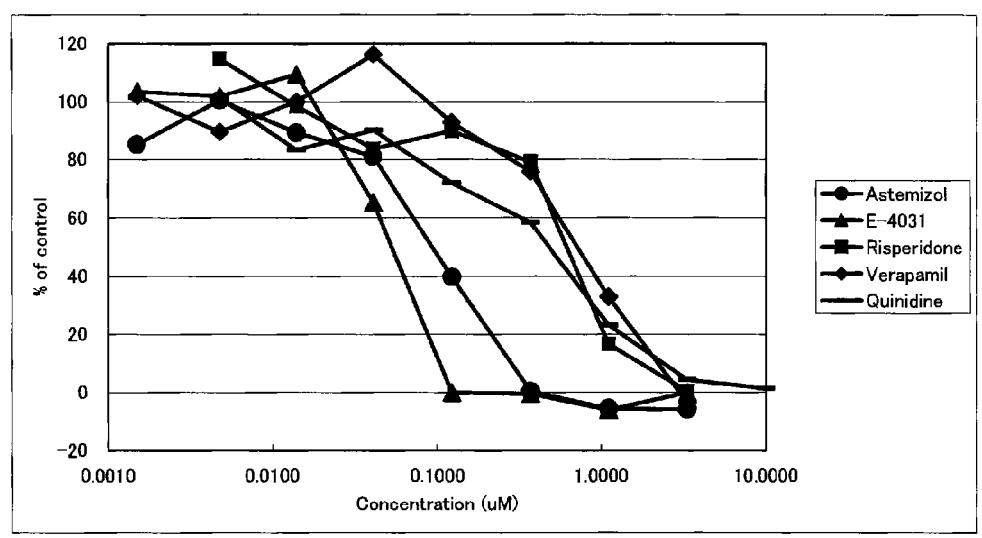
FIG. 18 shows the hERG inhibitory activities of known compounds at various concentrations.

The results revealed that, while most of the data points were missing in the cell strain into which hERG gene was transferred by lipofection, all the data could be obtained in the cell strain into which hERG gene was transferred with retrovirus. Also, the $IC_{50}$ values of individual drugs (0.083, 0.044, 0.536, 0.720 and 0.385 µM) could be obtained in the latter cell strain (FIG. 18).

Example 22

Measurement of Changes in Membrane Potential with FLIPR Membrane Potential Assay Kit This experiment was conducted on the cell strain into which hERG gene was transferred with retrovirus (Example 14) by using FLIPR Membrane Potential Assay Kit (Molecular Devices) and FDSS6000 (Hamamatsu Photonics). hERG channel-expressing cells were plated on Biocoat Poly-D-Lysine 384-Well Black/Clear Plate (BECKTON DICKINSON) two days before measurement. Briefly, a cell suspension was prepared to give a concentration of $1.2 \times 10^5$ cells/ml, and a 25 µl aliquot of this suspension was dispensed into each well. Component A contained in FLIPR Membrane Potential Assay Kit was dissolved in a measurement buffer (130 mM NaCl, 5 mM KCl, 1 mM $MgCl_2$, 1 mM $CaCl_2$, 24 mM Glucose, 10 mM HEPES (final pH: approx. 7.25)), and a 25 µl aliquot of this solution was added to each well. About one hour after the addition of Component A, changes in membrane potential were measured with FDSS6000. The measuring program was as follows: 10 times before the addition of a test substance, 50 times after the addition and at 6 second intervals. Measurement was performed at room temperature. hERG inhibitory activity was calculated from the fluorescence intensity change for 5 min after the addition of the test substance. As positive controls, E4031 and Dofetilide were used.

Figure 19:
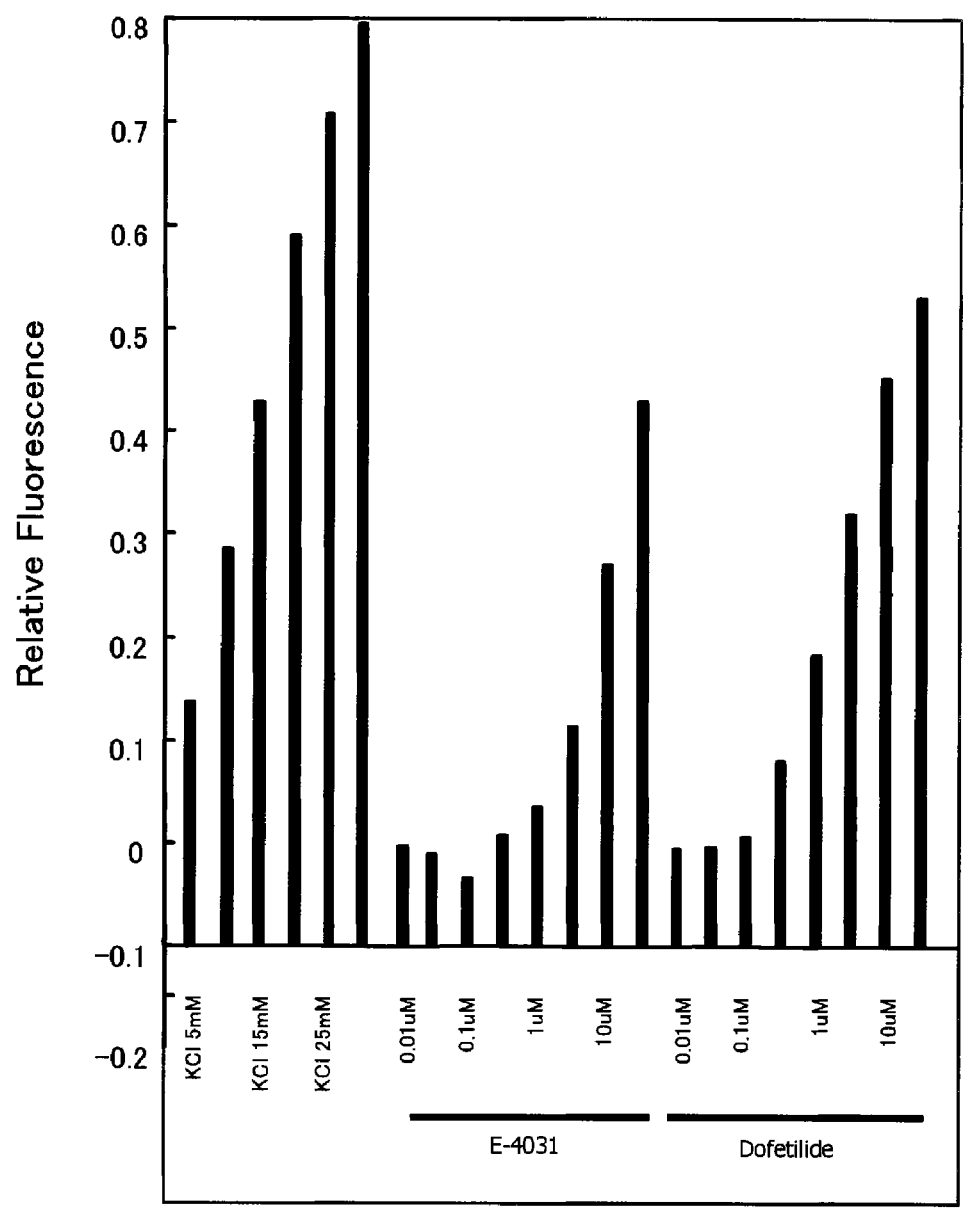
FIG. 19 shows changes in membrane potential caused by KCl, E4031 and Dofetilide which are hERG inhibitors.

The results are shown in FIG. 19. Changes in fluorescence intensity that mean the membrane potential was depolarized by the addition of KCl were observed. Similar changes in the membrane potential were also caused by E4031 and Dofetilide which are hERG inhibitors, and the changes depended on the concentration of these inhibitors.

Example 23

Recording of hERG Currents by Conventional Patch Clamp Technique

The recording of hERG currents by the conventional patch clamp technique was conducted by using the hERG-expressing cells of the present invention. The measurement of hERG currents was performed as described below with reference to Zhou, Z. et al., Biophysical Journal, 74, 230-241 (1998).

Cells were plated on polylysine-coated glass plates and cultured for 2 to 4 days. At measurement the resultant glass plates were transferred into a current measurement bath. hERG currents were observed by the voltage clamp method of the whole cell patch clamp technique. As solutions for recording of hERG currents, an extracellular perfusion solution (NaCl 137 mM, KCl 4 mM, $MgCl_2$ 1 mM, $CaCl_2$ 1.8 mM, glucose 10 mM, HEPES 10 mM, pH7.4) and an intraelectrode solution (KCl 130 mM, $MgCl_2$ 1 mM, Mg-ATP 5 mM, EGTA 5 mM, HEPES 10 mM, pH7.2) were used. For measuring hERG currents, a current amplifier (Axon Instruments) was used. For recording and analyzing hERG currents, pCLAMP software (Axon Instruments) was used. hERG currents were induced in cells by changing the potential from −80 mV to +20 mV for 5 sec and then to −50 mV for 4 sec, at 20 sec intervals. The peak value of the tail current observed when the potential was restored to −50 mV was used as the amplitude of hERG current.

INDUSTRIAL APPLICABILITY

According to the present invention, a method of establishing a cell with a remarkably high hERG channel expression level for use in predicting adverse effects based on hERG channel inhibition in research and development of drugs has been established. With this method, highly sensitive and high throughput evaluation has become possible.

Further, according to the present invention, hERG channel high expressing cells can be obtained simultaneously and efficiently. With this advantage, by allowing a wide variety of cell species to express hERG gene at high levels and comparing influences of endogenous ion channels among those cell species, it has become possible to select the most suitable cell species for predicting adverse effects in research and development of drugs. Further, the hERG channel-expressing cell or hERG channel-expressing cell population of the present invention is capable of expressing hERG channels stably for a long period of time.

SEQUENCE LISTING FREE TEXT

SEQ ID NO: 3: primer
SEQ ID NO: 4: primer
SEQ ID NO: 5: primer
SEQ ID NO: 6: primer
SEQ ID NO: 7: primer
SEQ ID NO: 8: primer
SEQ ID NO: 9: oligo DNA
SEQ ID NO: 10: oligo DNA
SEQ ID NO: 11: primer
SEQ ID NO: 12: primer The publications cited in the present specification are incorporated herein in their entirety.

What is claimed is:

1. A hERG channel-expressing cell population comprising cells capable of expressing a channel of which the hERG current as determined by patch clamping with a fully automated high throughput patch clamp system is 0.6 nA or more,
wherein the proportion of said cells is 40% or more relative to the total number of hERG gene-transferred cells within said population, and
wherein the hERG gene has been transferred with a retrovirus vector.

2. The cell population according to claim 1, wherein the average value of the hERG current in the total cell population is 0.3 nA or more.

3. A hERG channel-expressing cell population of claim 1, wherein the hERG current as determined by patch clamping with a fully automated high throughput patch clamp system is 1.0 nA or more.

4. A method of preparing the cell population according to claim 1, the method comprising expressing hERG channels via a retrovirus vector.

5. The method according to claim 4, the method further comprising the step of concentrating the virus vector by ultracentrifugation.

6. A method of measuring hERG current inhibitory activity, the method comprising using the cell population of claim 1.

7. The method according to claim 6, the method further comprising using a fully automated high throughput patch clamp system.

8. A method of measuring hERG current inhibitory activity, the method comprising using a cell population or a cell prepared by the method according to claim 4.

9. The method according to claim 8, the method further comprising using a fully automated high throughput patch clamp system.

10. A method of screening a compound or a salt thereof for its hERG current altering effect, the method comprising using a cell population according to claim 1.

11. The method according to claim 10, the method further comprising using a fully automated high throughput patch clamp system.

12. A method of screening a compound or a salt thereof for its hERG current altering effect, the method comprising using a cell population or a cell prepared by the method according to claim 4.

13. The method according to claim 12, the method further comprising using a fully automated high throughput patch clamp system.

14. A method of measuring hERG current inhibitory activity, the method comprising using the cell population according to claim 3.

15. A method of screening a compound or a salt thereof for its hERG current altering effect, the method comprising using the cell population according to claim 3.

* * * * *